US011434458B2

(12) United States Patent
Hinojosa et al.

(10) Patent No.: US 11,434,458 B2
(45) Date of Patent: Sep. 6, 2022

(54) SYSTEMS AND METHODS FOR IMPROVED PERFORMANCE OF FLUIDIC AND MICROFLUIDIC SYSTEMS

(71) Applicant: President and Fellows of Harvard College, Cambridge, MA (US)

(72) Inventors: Christopher David Hinojosa, Cambridge, MA (US); Josiah Sliz, Boston, MA (US); Daniel Levner, Cambridge, MA (US); Guy Thompson, Lexington, MA (US); Hubert Geisler, Saint-die-des-Vosges (FR); Jose Fernandez-Alcon, Cambridge, MA (US); Donald E. Ingber, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/403,942

(22) Filed: Jan. 11, 2017

(65) Prior Publication Data
US 2017/0121658 A1  May 4, 2017

Related U.S. Application Data

(63) Continuation of application No. PCT/US2015/040026, filed on Jul. 10, 2015.
(Continued)

(51) Int. Cl.
*C12M 3/06* (2006.01)
*B01L 3/00* (2006.01)
(Continued)

(52) U.S. Cl.
CPC ........... *C12M 23/16* (2013.01); *B01L 3/5027* (2013.01); *B01L 3/50273* (2013.01);
(Continued)

(58) Field of Classification Search
CPC ........ B01L 3/502715; B01L 2200/027; B01L 3/502746; B01L 3/502707;
(Continued)

(56) References Cited

U.S. PATENT DOCUMENTS

| 3,300,386 A | 1/1967 | Aron-Brunetiere |
| 3,313,290 A | 4/1967 | Chance |

(Continued)

FOREIGN PATENT DOCUMENTS

| JP | 2005-516220 A | 6/2005 |
| JP | 2009-109249 A | 5/2009 |

(Continued)

OTHER PUBLICATIONS

US 6,465,252 B1, 10/2002, Toner (withdrawn)
(Continued)

*Primary Examiner* — Jennifer Wecker
*Assistant Examiner* — Bryan Kilpatrick
(74) *Attorney, Agent, or Firm* — Nixon Peabody LLP

(57) ABSTRACT

Systems and methods for improved flow properties in fluidic and microfluidic systems are disclosed. The system includes a microfluidic device having a first microchannel, a fluid reservoir having a working fluid and a pressurized gas, a pump in communication with the fluid reservoir to maintain a desired pressure of the pressurized gas, and a fluid-resistance element located within a fluid path between the fluid reservoir and the first microchannel. The fluid-resistance element includes a first fluidic resistance that is
(Continued)

substantially larger than a second fluidic resistance associated with the first microchannel.

16 Claims, 13 Drawing Sheets

Related U.S. Application Data

(60) Provisional application No. 62/127,438, filed on Mar. 3, 2015, provisional application No. 62/024,361, filed on Jul. 14, 2014.

(51) Int. Cl.
  *B82Y 15/00* (2011.01)
  *C12M 1/34* (2006.01)
  *G01N 33/50* (2006.01)
  *C12M 3/00* (2006.01)
  *C12M 1/26* (2006.01)

(52) U.S. Cl.
  CPC ... *B01L 3/502715* (2013.01); *B01L 3/502746* (2013.01); *B82Y 15/00* (2013.01); *C12M 21/08* (2013.01); *C12M 33/12* (2013.01); *C12M 41/00* (2013.01); *C12M 41/40* (2013.01); *C12M 41/46* (2013.01); *G01N 33/5005* (2013.01); *B01L 2200/027* (2013.01); *B01L 2200/0605* (2013.01); *B01L 2200/0684* (2013.01); *B01L 2300/044* (2013.01); *B01L 2300/0681* (2013.01); *B01L 2300/0816* (2013.01); *B01L 2300/0864* (2013.01); *B01L 2300/0867* (2013.01); *B01L 2300/14* (2013.01); *B01L 2400/0487* (2013.01); *B01L 2400/084* (2013.01)

(58) Field of Classification Search
  CPC .......... B01L 3/502761; B01L 3/50273; B01L 3/5027; B01L 2300/0877; B01L 2300/0645; B01L 2400/082; B01L 9/52; B01L 2200/10; C12M 23/16; C12M 23/42; C12M 41/40; C12M 41/00; C12M 29/14; G01N 2500/10; G01N 33/50; G01N 15/0826; G01N 27/453; B01J 19/0093; B01J 2219/00813
  See application file for complete search history.

(56) References Cited

U.S. PATENT DOCUMENTS

| | | |
|---|---|---|
| 3,722,504 A | 3/1973 | Sawyer |
| 3,941,662 A | 3/1976 | Munder |
| 3,948,732 A | 4/1976 | Haddad |
| 4,225,671 A | 9/1980 | Puchinger |
| 4,436,824 A | 3/1984 | Bishop |
| 4,446,229 A | 5/1984 | Indech |
| 4,537,860 A | 8/1985 | Tolbert |
| 4,610,878 A | 9/1986 | Wilson |
| 4,629,686 A | 12/1986 | Gruenberg |
| 4,650,766 A | 3/1987 | Harm |
| 4,673,650 A | 6/1987 | Braden |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer |
| 4,835,102 A | 5/1989 | Bell |
| 4,839,280 A | 6/1989 | Banes |
| 4,851,354 A | 7/1989 | Winston |
| 4,929,542 A | 5/1990 | Risley |
| 4,940,853 A | 7/1990 | Vandenburgh |
| 5,002,890 A | 3/1991 | Morrison |
| 5,043,260 A | 4/1991 | Jauregui |
| 5,108,926 A | 4/1992 | Klebe |
| 5,160,490 A | 11/1992 | Naughton |
| 5,197,575 A | 3/1993 | Mangum et al. |
| 5,217,899 A | 6/1993 | Shapiro |
| 5,290,684 A | 3/1994 | Kelly |
| 5,316,905 A | 5/1994 | Mori |
| 5,348,879 A | 9/1994 | Shapiro |
| 5,486,335 A | 1/1996 | Wilding |
| 5,496,697 A | 3/1996 | Parce |
| 5,498,392 A | 3/1996 | Wilding |
| 5,587,128 A | 12/1996 | Wilding |
| 5,612,188 A | 3/1997 | Shuler |
| 5,637,469 A | 6/1997 | Wilding |
| 5,645,432 A | 7/1997 | Jessop |
| 5,726,026 A | 3/1998 | Wilding |
| 5,744,366 A | 4/1998 | Kricka |
| 5,750,329 A | 5/1998 | Quinn |
| 5,820,769 A | 10/1998 | Chou |
| 5,900,160 A | 5/1999 | Whitesides |
| 5,906,828 A | 5/1999 | Cima |
| 6,048,723 A | 4/2000 | Banes |
| 6,054,277 A | 4/2000 | Furcht |
| 6,133,030 A | 10/2000 | Bhatia |
| 6,197,575 B1 | 3/2001 | Griffith |
| 6,255,106 B1 | 7/2001 | Marx |
| 6,306,644 B1 | 10/2001 | Marx |
| 6,329,195 B1 | 12/2001 | Pfaller |
| 6,454,924 B2 | 9/2002 | Jedrzejewski |
| 6,472,202 B1 | 10/2002 | Banes |
| 6,500,151 B1 * | 12/2002 | Cobb ................ A61M 5/14566 604/131 |
| 6,530,370 B1 | 3/2003 | Heinonen |
| 6,562,616 B1 | 5/2003 | Toner |
| 6,586,235 B1 | 7/2003 | Banes |
| 6,630,801 B2 | 10/2003 | Schuurmans |
| 6,645,759 B2 | 11/2003 | Banes |
| 6,653,124 B1 | 11/2003 | Freeman |
| 6,730,516 B2 | 5/2004 | Jedrzejewski |
| 6,921,253 B2 | 7/2005 | Shuler |
| 6,998,265 B2 | 2/2006 | Banes |
| 7,049,057 B2 | 5/2006 | Atala |
| 7,288,405 B2 | 10/2007 | Shuler |
| 7,314,718 B1 | 1/2008 | Dasgupta |
| 7,438,856 B2 | 10/2008 | Jedrzejewski |
| 7,745,209 B2 | 6/2010 | Martin |
| 7,763,456 B2 | 7/2010 | Li |
| 7,790,028 B1 | 9/2010 | Weinberg |
| 7,960,166 B2 | 6/2011 | Vacanti |
| 7,964,078 B2 | 6/2011 | Lee |
| 7,976,795 B2 | 7/2011 | Zhou |
| 7,977,089 B2 | 7/2011 | Wikswo |
| 7,985,336 B2 | 7/2011 | Weinberg |
| 7,999,937 B1 | 8/2011 | Srivastava |
| 8,030,061 B2 | 10/2011 | Shuler |
| 8,147,562 B2 | 4/2012 | Vacanti |
| 8,187,863 B2 | 5/2012 | Sim |
| 8,268,152 B2 | 9/2012 | Stelzle |
| 8,273,572 B2 | 9/2012 | Martin |
| 8,318,479 B2 | 11/2012 | Domansky |
| 8,343,740 B2 | 1/2013 | Gonda |
| 8,357,528 B2 | 1/2013 | Vacanti |
| 8,460,546 B2 | 6/2013 | Weinberg |
| 8,470,589 B2 | 6/2013 | Martin |
| 8,647,861 B2 | 2/2014 | Ingber |
| 2002/0129813 A1 | 9/2002 | Litherland |
| 2002/0173033 A1 | 11/2002 | Hammerick |
| 2002/0187560 A1 | 12/2002 | Pezzuto |
| 2003/0021792 A1 | 1/2003 | Roben |
| 2003/0082795 A1 | 5/2003 | Shuler |
| 2003/0096405 A1 | 5/2003 | Takayama |
| 2003/0175824 A1 | 9/2003 | Pishko |
| 2004/0034435 A1 | 2/2004 | Atala |
| 2004/0115731 A1 | 6/2004 | Hansen |
| 2004/0132166 A1 | 7/2004 | Miller |
| 2004/0181343 A1 | 9/2004 | Wigstrom |
| 2005/0005684 A1 | 1/2005 | Chien |
| 2005/0032205 A1 | 2/2005 | Smith |
| 2005/0169962 A1 | 8/2005 | Bhatia |
| 2005/0266393 A1 | 12/2005 | Baxter |

(56) References Cited

U.S. PATENT DOCUMENTS

| | | |
|---|---|---|
| 2005/0273995 A1 | 12/2005 | Kanagasabapathi |
| 2006/0019326 A1 | 1/2006 | Vacanti |
| 2006/0099116 A1 | 5/2006 | Manger |
| 2006/0154361 A1 | 7/2006 | Wikswo |
| 2006/0263336 A1 | 11/2006 | Caplan |
| 2006/0270023 A1 | 11/2006 | LeDuc |
| 2007/0015273 A1 | 1/2007 | Shuler |
| 2007/0015274 A1 | 1/2007 | Shuler |
| 2007/0015275 A1 | 1/2007 | Shuler |
| 2007/0020693 A1 | 1/2007 | Shuler |
| 2007/0026519 A1 | 2/2007 | Shuler |
| 2007/0037273 A1 | 2/2007 | Shuler |
| 2007/0037275 A1 | 2/2007 | Shuler |
| 2007/0037277 A1 | 2/2007 | Shuler |
| 2007/0048727 A1 | 3/2007 | Shuler |
| 2007/0122794 A1 | 5/2007 | Shuler |
| 2007/0122896 A1 | 5/2007 | Shuler |
| 2007/0144514 A1 | 6/2007 | Yeates |
| 2007/0155019 A1 | 7/2007 | Johnson |
| 2007/0157973 A1 | 7/2007 | Chien |
| 2007/0172943 A1 | 7/2007 | Freedman |
| 2007/0207194 A1 | 9/2007 | Grayburn |
| 2007/0224677 A1 | 9/2007 | Neumann |
| 2007/0243627 A1 | 10/2007 | Takayama |
| 2007/0275435 A1 | 11/2007 | Kim |
| 2007/0275455 A1 | 11/2007 | Hung |
| 2007/0275882 A1 | 11/2007 | Meijer |
| 2007/0281353 A1 | 12/2007 | Vacanti |
| 2008/0032380 A1 | 2/2008 | Kleis |
| 2008/0038839 A1* | 2/2008 | Linder ............ G01N 33/54386 436/501 |
| 2008/0064088 A1 | 3/2008 | Shuler |
| 2008/0166794 A1 | 7/2008 | Shuler |
| 2008/0166795 A1 | 7/2008 | Shuler |
| 2008/0181829 A1 | 7/2008 | Matteo |
| 2008/0233607 A1 | 9/2008 | Yu |
| 2008/0318334 A1 | 12/2008 | Robotti |
| 2009/0028755 A1 | 1/2009 | Jedrzejewski |
| 2009/0074623 A1 | 3/2009 | Park |
| 2009/0078614 A1 | 3/2009 | Varghese |
| 2009/0131858 A1 | 5/2009 | Fissell |
| 2009/0134235 A1 | 5/2009 | Ivr |
| 2009/0220932 A1 | 9/2009 | Ingber |
| 2010/0041128 A1 | 2/2010 | Banes |
| 2010/0043494 A1 | 2/2010 | Gascon |
| 2010/0267136 A1 | 10/2010 | Vacanti |
| 2010/0288382 A1 | 11/2010 | Levent |
| 2010/0294986 A1 | 11/2010 | Sultana |
| 2010/0304355 A1 | 12/2010 | Shuler |
| 2010/0323439 A1 | 12/2010 | Takayama |
| 2011/0000482 A1 | 1/2011 | Gumaste |
| 2011/0027804 A1 | 2/2011 | Yarmush |
| 2011/0053207 A1 | 3/2011 | Hoganson |
| 2011/0086382 A1 | 4/2011 | Marx |
| 2011/0120871 A1* | 5/2011 | Reid ................ G01N 33/48721 204/540 |
| 2011/0180150 A1 | 7/2011 | Cooksey |
| 2011/0183312 A1 | 7/2011 | Huang |
| 2011/0250585 A1 | 10/2011 | Ingber |
| 2011/0269226 A1 | 11/2011 | Van Noort |
| 2011/0287469 A1 | 11/2011 | Guenther |
| 2012/0003732 A1 | 1/2012 | Hung |
| 2012/0088693 A1 | 4/2012 | Lee |
| 2012/0135446 A1 | 5/2012 | Collins |
| 2012/0135452 A1 | 5/2012 | Shuler |
| 2012/0199487 A1 | 8/2012 | Stelzle |
| 2012/0214189 A1 | 8/2012 | Shuler |
| 2012/0318726 A1 | 12/2012 | Charest |
| 2012/0322097 A1 | 12/2012 | Charest |
| 2013/0059322 A1 | 3/2013 | Hung |
| 2013/0109594 A1 | 5/2013 | Gonda |
| 2013/0171679 A1 | 7/2013 | Lee |
| 2013/0320999 A1 | 12/2013 | Deane |
| 2014/0038279 A1 | 2/2014 | Ingber |
| 2014/0158233 A1 | 6/2014 | Leslie |
| 2014/0186414 A1 | 7/2014 | Ingber |
| 2014/0199764 A1 | 7/2014 | Domansky |
| 2014/0342445 A1 | 11/2014 | Ingber |
| 2015/0004077 A1 | 1/2015 | Wikswo |
| 2015/0079670 A1 | 3/2015 | Domansky |
| 2015/0209783 A1 | 7/2015 | Ingber |
| 2015/0306596 A1 | 10/2015 | Thompson |
| 2016/0121329 A1 | 5/2016 | Kinahan |

FOREIGN PATENT DOCUMENTS

| | | |
|---|---|---|
| WO | WO 2009/157863 A1 | 12/2009 |
| WO | WO 2010/009307 A3 | 7/2010 |
| WO | WO 2013/014216 A1 | 1/2013 |
| WO | WO 2013/085909 A1 | 6/2013 |
| WO | WO 2014/039517 A1 | 3/2014 |
| WO | WO 2014/107240 A1 | 7/2014 |
| WO | WO 2014/210364 A2 | 12/2014 |
| WO | WO 2015/006751 A1 | 1/2015 |
| WO | WO 2015/013332 A1 | 1/2015 |
| WO | WO 2015/138032 A2 | 9/2015 |
| WO | WO 2015/138034 A1 | 9/2015 |

OTHER PUBLICATIONS

International Search Report, PCT/US15/40026, dated Oct. 13, 2015 (2 pages).
Written Opinion of the International Searching Authority, PCT/US15/40026, dated Oct. 13, 2015 (9 pages).
Cooksey, G. A. et al., "A multi-purpose microfluidic perfusion system with combinatorial choice of inputs, mixtures, gradient patterns, and flow rates," Lab on a, Royal Society of Chemistry 9, pp. 417-426, Jan. 1, 2009.
Wu, M. et al., "Microfluidic cell culture systems for drug research," Lab on a Chip, 10(8):939-951, Jan. 1, 2010.
Tehranirokh, M. et al., "Microfluidic devices for cell cultivation and proliferation," Biomicrofluidics, 7(5):51502-1, Sep. 1, 2013.
Extended European Search Report in European Patent Application No. EP 15822409.7, dated Mar. 6, 2018 (3 pages).

* cited by examiner

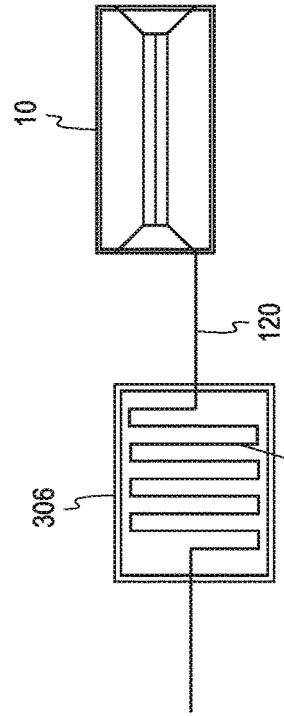
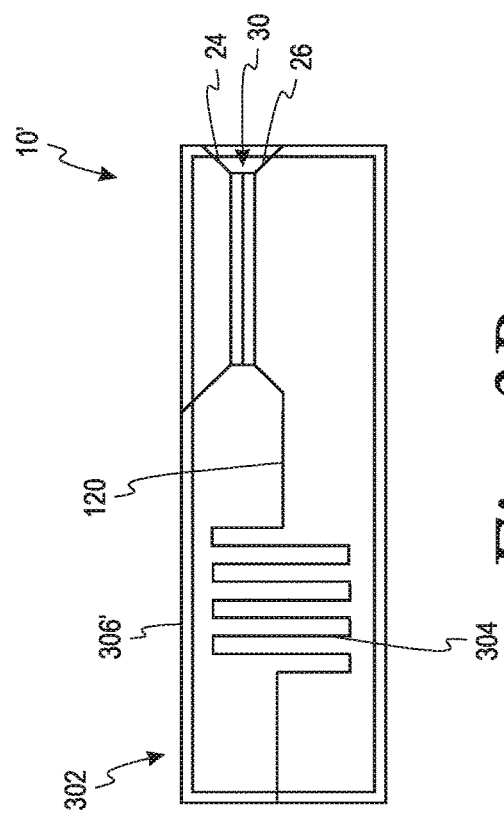

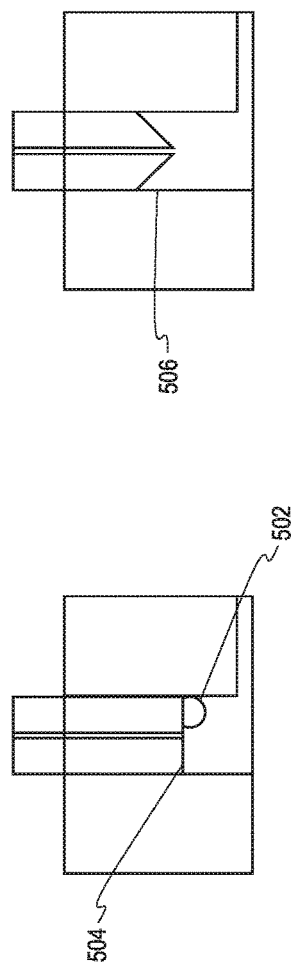
*Fig. 5A*
*Fig. 5B*
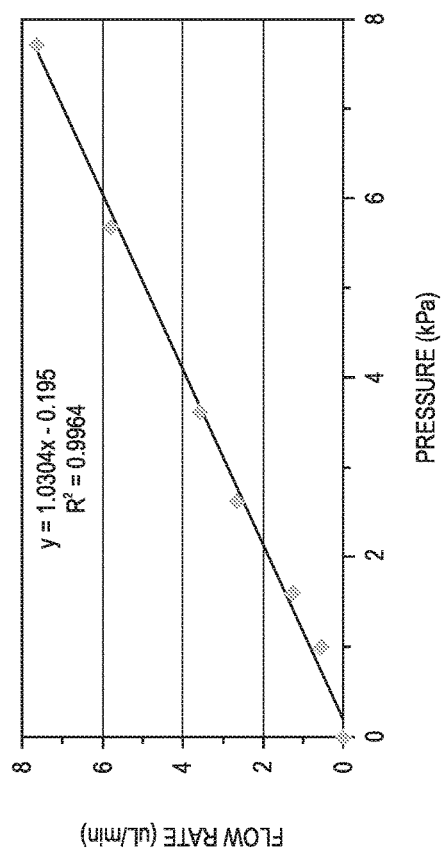
*Fig. 6*

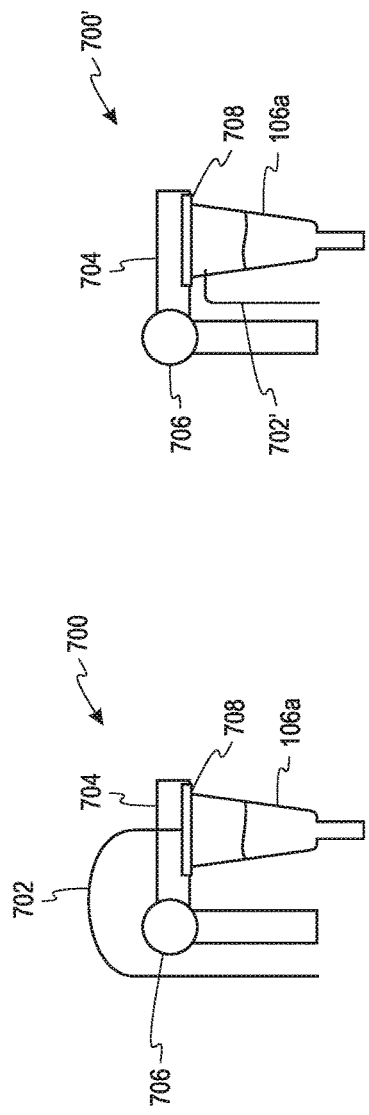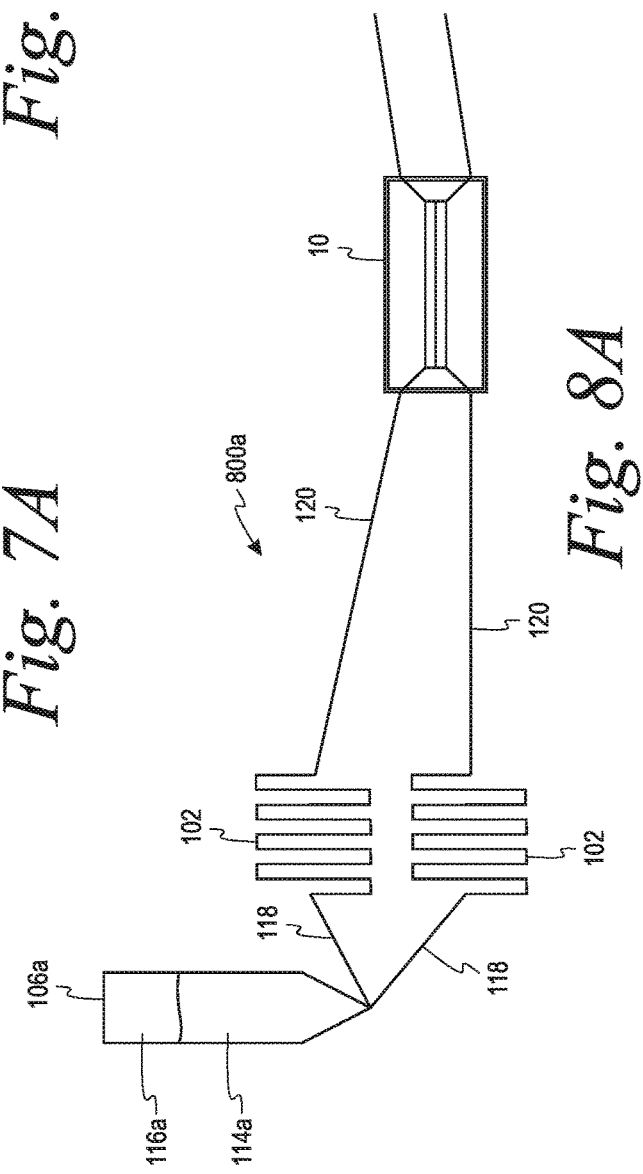

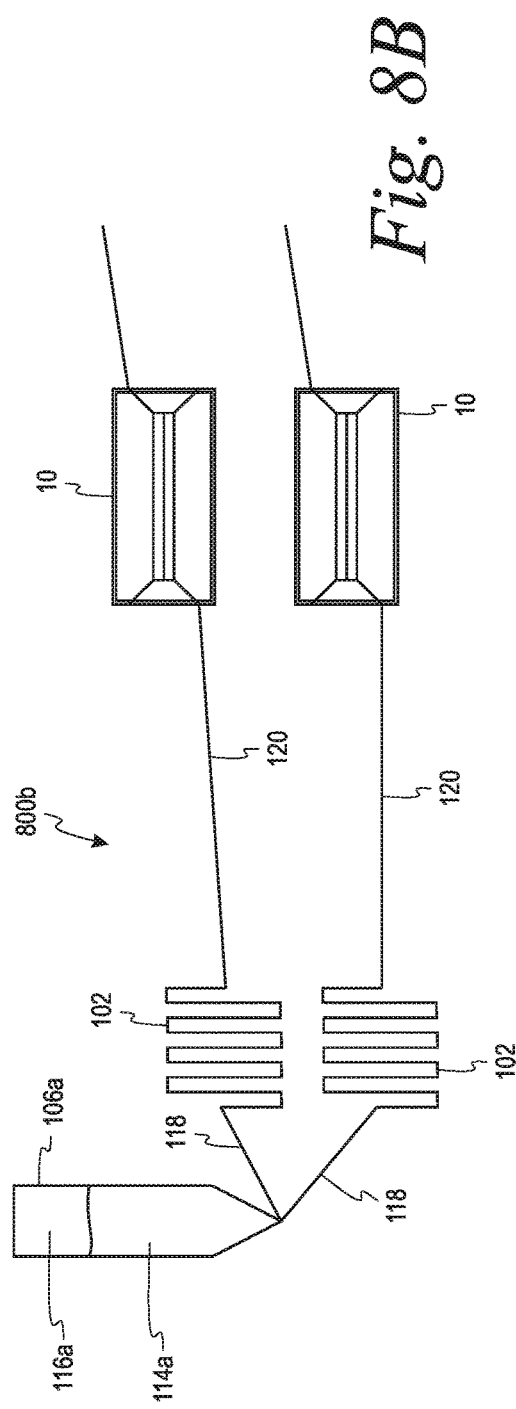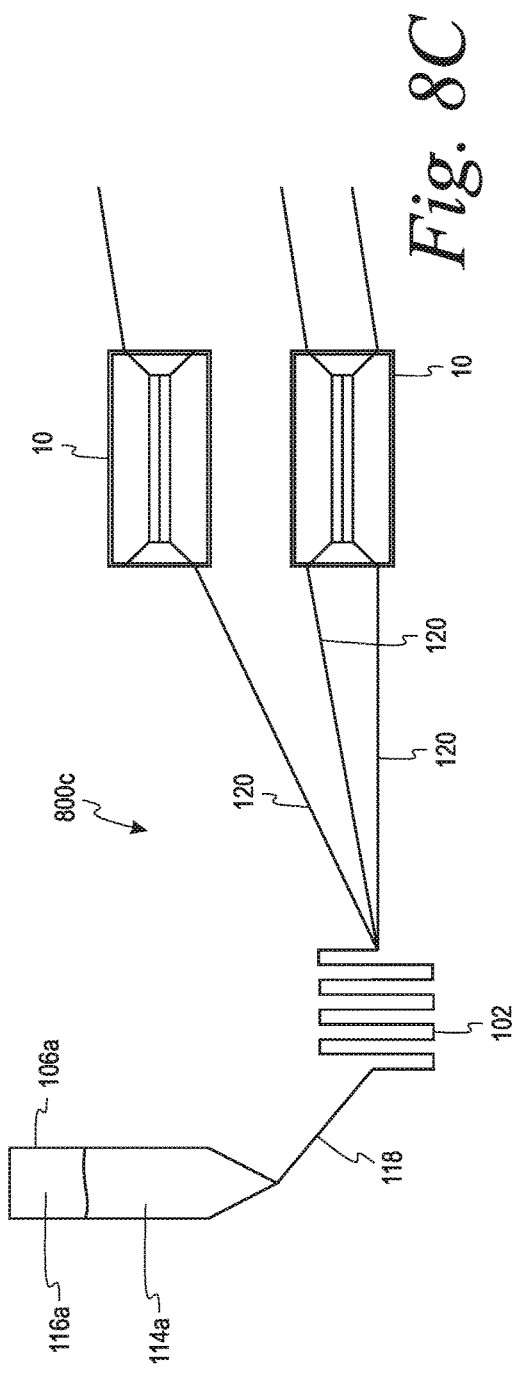

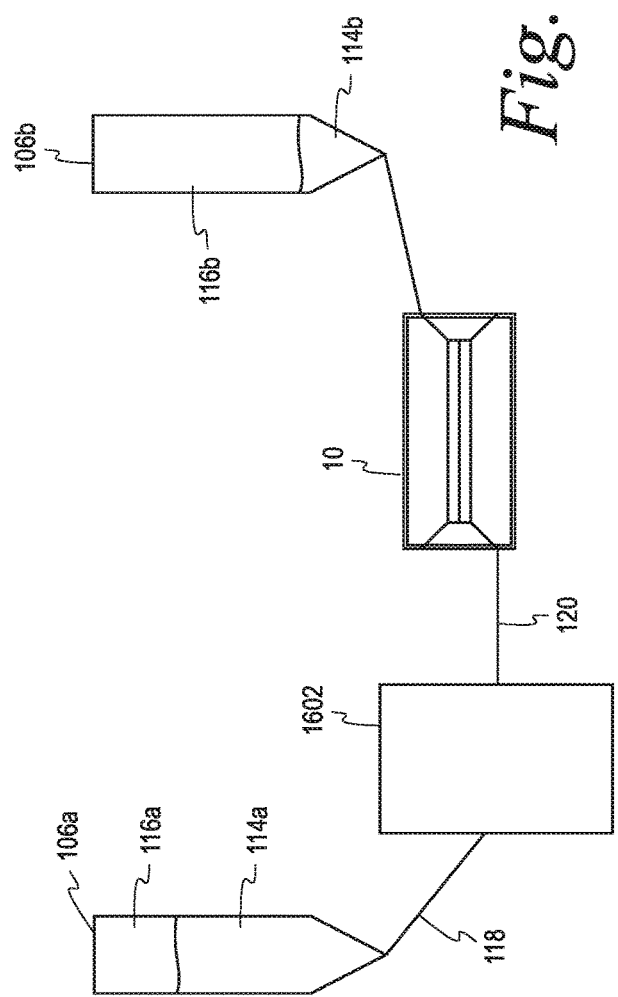
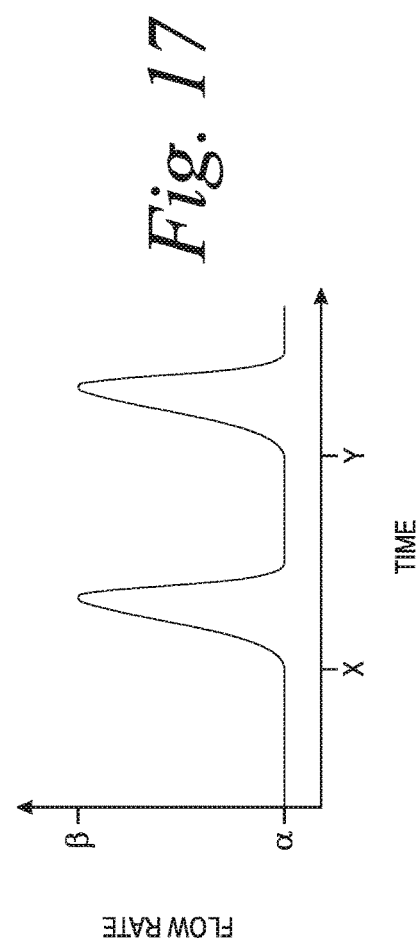

SYSTEMS AND METHODS FOR IMPROVED PERFORMANCE OF FLUIDIC AND MICROFLUIDIC SYSTEMS

CROSS-REFERENCE TO RELATED APPLICATIONS

This application is a continuation of International Application No. PCT/US15/040026, filed Jul. 10, 2015, which claims priority to U.S. Provisional Application No. 62/127,438, filed Mar. 3, 2015, and U.S. Provisional Application No. 62/024,361, filed Jul. 14, 2014, each of which is herein incorporated by reference in its entirety.

GOVERNMENT SUPPORT

This invention was made with government support under grant no. W911NF-12-2-0036 awarded by U.S. Department of Defense, Advanced Research Projects Agency. The government has certain rights in the invention.

TECHNICAL FIELD

The present invention relates to fluidic and microfluidic systems. Specifically, the invention relates to systems and methods for providing improved flow properties in fluidic and microfluidic systems.

BACKGROUND

Microfluidic devices for cell culture typically need to be perfused with fluid media at an extremely low flow rate, such as between 30 μL/hr and 5 mL/hr. Moreover, in some experiments, the media must be flowed at known rates for several weeks. Additionally, many experiments need tens of channels to be able to explore a number of test conditions, in order to gain statistically significant results. Therefore, the devices are preferably tested simultaneously using the same setup. What is more, the footprint of the perfusion system must be small enough to allow for the integration of many devices (e.g., at least 12 devices) in a reasonable space.

Some existing technologies attempt to solve fluid-flow issues using rollers on a stepper motor to engage an elastic polymer with channels in it. As the motor spins, it pushes the fluid through the cartridge and the chips. This pumping scheme, however, cannot be sufficiently minimized. Additionally, because the pumping mechanism must be engaged with the cartridge, the pump-head must reside inside an incubated space. Finally, the microfluidic peristaltic pumping system relies on a material that must be resistant to frictional/shearing forces, have a low elastic modulus, be injection moldable or otherwise mass producible, be bondable (to allow creating microfluidic channels), be non-cytotoxic, and not absorb or substantially adsorb small molecules. To date, it appears that there is no such material that sufficiently meets all of these demands.

Other alternative pumping technologies are traditional peristaltic pumps and syringe pumps. Traditional peristaltic pumps tend to be bulky, and they require specialized tubing to be strung up through the pump before each use. In turn, the tubing needed to attain the low flow-rates typical of organs-on-chips is difficult to connectorize and assemble with chips or cartridges. Syringe pumps are also bulky, and they provide no simple way to change out syringes after the entire syringe volume has been discharged.

Further, accumulation of gas bubbles poses risks to microfluidic systems and components thereof. Gas bubbles can have many detrimental effects when introduced into or formed inside of microfluidic channels. For example, large capillary forces that are characteristic of bubble interfaces confined to small dimensions can cause difficulty in removing bubbles from the microfluidic channels. In microfluidic devices that include cells, gas bubbles can be especially detrimental for several additional reasons. For example, stagnant bubbles sitting on top of the cells can starve them of critical nutrients. Further, even when only passing by cells, bubbles can damage the cells due to high shear and capillary forces (e.g., by delaminating the cell layer). Many methods have been proposed for preventing bubbles from entering microfluidic devices or being formed within the devices. However, it is very difficult to completely prevent bubble-generation events or bubble-accumulation events within a microfluidic system. Thus, it is unlikely that bubbles will be fully eliminated over the duration of a long-term experiment.

Aspects of the present invention provide new fluid-pumping systems and methods for microfluidic devices that provide a consistent and reliable flow of media to the microchannels and/or provide systems and methods for preventing, inhibiting, or limiting damage caused by bubbles that are generated or accumulated.

SUMMARY

According to aspects of the present invention, a system for monitoring a biological function associated with cells includes a microfluidic device, a fluid line, and a fluid-resistance element. The microfluidic device includes a first microchannel, a second microchannel, and a membrane located at an interface region between the first microchannel and the second microchannel. The membrane includes a first side facing toward the first microchannel and a second side facing toward the second microchannel. The first side includes the cells adhered thereto, and the second side may also include the same or different cells adhered thereto. The fluid line is for delivering a working fluid to or from the first microchannel from a fluid reservoir. The fluid-resistance element is coupled to the fluid line, although it may also be coupled to a fluid-output line leading away from the microfluidic device. The fluid-resistance element includes a first fluidic resistance that is substantially larger than a second fluidic resistance associated with the first microchannel.

According to further aspects of the present invention, a device for monitoring a biological function associated with cells includes a body. The body includes a first microchannel, a second microchannel, and a membrane located at an interface region between the first microchannel and the second microchannel. The membrane includes a first side facing toward the first microchannel and a second side facing toward the second microchannel. The first side includes the cells adhered thereto. The body further defines an internal fluid-resistance element coupled to the first microchannel. The internal fluid-resistance element having a first fluidic resistance that is substantially larger than a second fluidic resistance associated with the first microchannel.

According to further aspects of the present invention, a system for monitoring a biological function associated with cells includes a microfluidic device, a fluid reservoir, a pump mechanism, and a fluid resistance element. The microfluidic device includes a first microchannel, a second microchannel, and a membrane located at an interface region between the first microchannel and the second microchannel. The membrane includes a first side facing toward the first microchannel and a second side facing toward the second microchannel, the first side having the cells adhered thereto. The fluid reservoir includes a working fluid and a pressurized gas. The pump mechanism is in communication with the fluid reservoir to maintain a desired pressure of the pressurized gas. The fluid-resistance element is located within a fluid path between the fluid reservoir and the first microchannel. The fluid-resistance element includes a first fluidic resistance that is substantially larger than a second fluidic resistance associated with the first microchannel.

According to further aspects of the present invention, a system for monitoring a biological function associated with cells includes a microfluidic device, a fluid reservoir, a pressure regulator, and a sensor. The microfluidic device includes a first microchannel, a second microchannel, and a membrane located at an interface region between the first microchannel and the second microchannel. The membrane includes a first side facing toward the first microchannel and a second side facing toward the second microchannel. The first side includes the cells adhered thereto. The fluid reservoir includes a working fluid and a pressurized gas. The fluid reservoir is coupled to the first microchannel via a fluid line. The pressure regulator is in communication with the fluid reservoir to maintain a desired pressure of the pressurized gas. The pressurized gas causes the working fluid to move through the first microchannel. The sensor is for monitoring the activity of the pressure regulator to determine an increase in fluidic resistance within the fluid line or the first microchannel.

According to further aspects of the present invention, a system for monitoring a biological function associated with cells includes a microfluidic device, a fluid reservoir, a volumetric pump, and a sensor. The microfluidic device includes a first microchannel, a second microchannel, and a membrane located at an interface region between the first microchannel and the second microchannel. The membrane includes a first side facing toward the first microchannel and a second side facing toward the second microchannel. The first side includes the cells adhered thereto. The fluid reservoir includes a working fluid and a pressurized gas. The fluid reservoir is coupled to the first microchannel via a fluid line. The volumetric pump is in communication with the fluid reservoir to cause a pressure on the pressurized gas. The pressurized gas causes the working fluid to move through the first microchannel. The sensor is located between the fluid reservoir and the volumetric pump. The sensor is for monitoring the pressure of a gas in the system. In response to the pressure being below a predetermined value, the volumetric pump supplies gas to the fluid reservoir at a first volumetric flow rate. In response to the pressure being at or above the predetermined value, the volumetric pump supplies gas to the fluid reservoir at a second volumetric flow rate. The second volumetric flow rate is less than the first volumetric flow rate.

According to further aspects of the present invention, a system for monitoring a biological function associated with cells includes a microfluidic device, a fluid reservoir, and a pressure source. The microfluidic device includes a first microchannel, a second microchannel, and a membrane located at an interface region between the first microchannel and the second microchannel. The membrane includes a first side facing toward the first microchannel and a second side facing toward the second microchannel. The first side includes the cells adhered thereto. The fluid reservoir includes a working fluid and a pressurized gas. The fluid reservoir is coupled to the first microchannel via a fluid line. The pressurized gas causes the working fluid to move through the first microchannel. The pressure source in communication with the fluid reservoir to provide a modulated pressure profile, the modulated pressure profile including periodic pressure increases to inhibit the accumulation of bubbles in the system.

According to further aspects of the present invention, a microfluidic system includes a microfluidic device, a fluid reservoir, a fluid input line, and a fluid-resistance element. The microfluidic device includes a first microchannel. The fluid line is for delivering a working fluid to or from the first microchannel from the fluid reservoir. The fluid-resistance element is within the fluid line. The fluid-resistance element includes a first fluidic resistance that is substantially larger than a second fluidic resistance associated with the first microchannel.

According to further aspects of the present invention, a microfluidic system includes a microfluidic device having a first microchannel, a fluid reservoir having a working fluid and a pressurized gas, a pump in communication with the fluid reservoir to maintain a desired pressure of the pressurized gas, and a fluid-resistance element located within a fluid path between the fluid reservoir and the first microchannel. The fluid-resistance element includes a first fluidic resistance that is substantially larger than a second fluidic resistance associated with the first microchannel.

According to yet further aspects of the present invention, a system for monitoring a biological function associated with cells includes a microfluidic device, a pressure source, and a controller. The microfluidic device includes a microchannel. The microchannel includes a surface. The cells are adhered to the surface. The pressure source is configured to cause a working fluid to flow along a fluid path that includes the first microchannel of the microfluidic device. The controller is coupled to the pressure source and causes the pressure source to be operable in a normal operating mode and a flushing mode. The normal operating mode includes the working fluid flowing past the cells within the microchannel at a first flow rate. The flushing mode includes the working fluid flowing past the cells within the microchannel at a second flow rate that is higher than the first flow rate to move an undesired aggregation of bubbles from a first position in the fluid path toward a second position along the fluid path. The controller switches to the flushing mode in response to a predetermined condition.

According to still yet further aspects of the present invention, a method for monitoring a biological function associated with living cells includes flowing a working fluid at known fluid-flow conditions along a fluid path during a normal operating mode and, on a periodic basis during the normal operating mode, automatically flushing the fluid path at a flushing flow rate for a time period to remove at least a portion of an undesired aggregation from the fluid path. The fluid path includes a microchannel of a microfluidic device. The microchannel includes cells disposed therein.

Further methods of using these systems are disclosed below and in the claims.

These and other capabilities of the invention, along with the invention itself, will be more fully understood after a review of the following figures, detailed description, and claims.

BRIEF DESCRIPTION OF THE DRAWINGS

FIG. 3A is a schematic representation of a fluid-resistance element that is separate from the organ-on-chip device, according to aspects of the present disclosure.

FIG. 3B is a schematic representation of a fluid-resistance element that is a part of the organ-on-chip device, according to aspects of the present disclosure.

FIG. 5A illustrates an interface including a blunt-end tube that is used in the microfluidic system.

FIG. 5B illustrates an interface including a sharpened-tip tube that is used in the microfluidic system.

FIG. 6 is a flow-rate correlation graph of an example microfluidic system, according to aspects of the present disclosure.

FIG. 7A illustrates a moveable-cap assembly having a pressure line disposed therethrough, for use in the microfluidic system.

FIG. 7B illustrates a moveable-cap assembly having a pressure line disposed within the reservoir for use in the microfluidic system.

FIG. 8A is a schematic diagram of a microfluidic system having two fluid-resistance elements, each operatively coupled to a corresponding microfluidic channel of a single organ-on-chip device.

FIG. 8B is a schematic diagram of a microfluidic system having two fluid-resistance elements, each operatively coupled to a microfluidic channel of separate organ-on-chip devices.

FIG. 8C is a schematic diagram of a microfluidic system having one fluid-resistance element operatively coupled to multiple microfluidic channels.

FIG. 16 illustrates one embodiment of an exemplary system having a pressure source disposed between the input reservoir and the organ-on-chip device.

FIG. 17 illustrates an example flow profile having periodic flushing according to aspects of the present disclosure.

Figure 1B:
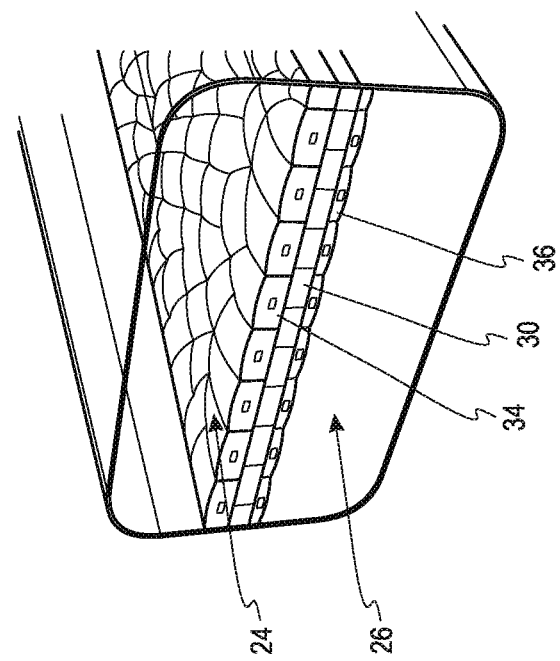
FIG. 1B illustrates a first and second microchannel of the organ-on-chip device of FIG. 1A.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Additionally, the singular terms "a," "an," and "the" include plural referents unless context clearly indicates otherwise.

Aspects of the present invention relate to a pressure-driven system that provides smooth and reliable fluid flow through a microfluidic device or devices. This pressure-driven system can utilize off-the-shelf, electronically controllable pressure regulators that can provide compact and long-lived actuation. Moreover, because the pumping action is transmitted by gas pressure, the modality enables designs wherein the bulk of the pumping system can remain both off the microfluidic device and off a cartridge that may hold one or more microfluidic devices, while not contacting biological liquids. This is an important advantage, because it can greatly simplify cartridge design, as well as reduce instrument sterility or contamination concerns.

Additionally or alternatively, aspects of the present invention relate to systems and methods that prevent, inhibit, or limit damage caused by bubbles that form within the microfluidic system, providing for long-term experimentation without significant loss, damage, or degradation of components (e.g., cells) within the microfluidic device. Damage caused by bubbles is prevented, inhibited, or limited through use of automated fluid-flushing of the microfluidic devices using periodically increased flow rates. Surprisingly, automated periodic flushing is not only successful in removing accumulated bubbles from the microfluidic system, but is also successful in preventing or inhibiting the bubbles from growing, accumulating, or coalescing as they otherwise do.

Another benefit of the periodic flushing is that, to the extent bubbles develop, they are smaller-sized bubbles, which lessens the opportunity for the bubbles to damage microfluidic devices or become pinned further downstream. This is especially beneficial in, for example, cell microfluidic cell-culture devices and organ-on-chip ("OOC") devices because smaller bubbles flowing through the microchannels reduce the risk of damage to the cells through, for example, delamination. Moreover, if a smaller bubble does become pinned to the surface of a cell, it is less likely to cause the death of that cell because nutrients may still be readily available to uncovered portions of the cell, or may be able to permeate to the cell through non-direct paths. Beneficially, periodic flushing allows for removal of bubbles without causing damage to the cells or organ-level function of the OOC device and/or system.

The periodic flushing function of the system also may be used to deliver a brief bolus of stimulus, drug, cytokine or nutrient or other molecular or chemical factor in physiological studies carried out using the OOC device 10.

Figure 1A:
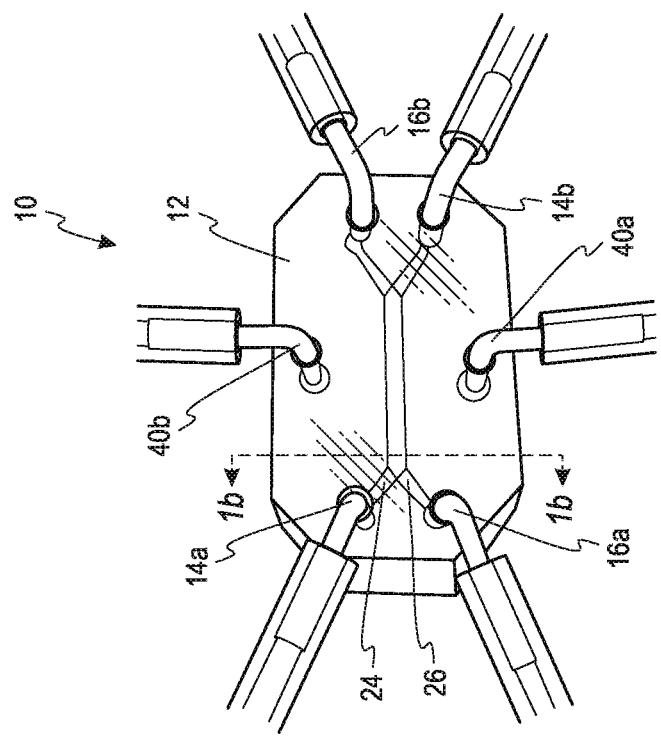
FIG. 1A illustrates an example organ-on-chip device that may be used with the fluid-pumping system of the present invention.

FIGS. 1A and 1B illustrate one type of an OOC device 10. The OOC device 10 includes a body 12 that is typically made of a polymeric material. The body 12 includes a first fluid inlet 14a and a first fluid outlet 14b. The body 12 further includes a second fluid inlet 16a and a second fluid outlet 16b. The first fluid inlet 14a and the first fluid outlet 14b permit a fluid to passed through a first microchannel 24. The second fluid inlet 16a and the second fluid outlet 16b permit fluid to passed through a second microchannel 26. The first microchannel 24 is separated from the second microchannel 26 by a membrane 30 at the interface region. The membrane 30 may include a first cell layer 34 on one side and a second cell layer 36 on the opposing side. Often, the first cell layer 34 is one type of cell while the second cell layer 36 is a second type of cell. The fluid moving through the first microchannel 24 and exposed to the first cell layer 34 may be the same as, or different from, the fluid moving through the second microchannel 26 and exposed to the second cell layer 36.

Depending on the application, the membrane 30 may have a porosity to permit the migration of cells, particulates, proteins, chemicals and/or media between the first cell layer 32 and the second cell layer 36. The membrane 30 is preferably flexible and elastic, allowing it to be controllably stretched during use so as to understand the influence of physiological forces on the the first cell layer 32 and the second cell layer 36. As shown in FIG. 1A, the body 12 includes two ports 40a and 40b that allow for a pressure differential within the body 12, thereby causing controlled movement of the membrane 30. More details on the OOC device 10 can be found in U.S. Pat. No. 8,647,861, which is owned by the assignee of the present application and is incorporated by reference in its entirety.

The fluidic resistance of the OOC device 10 is typically very low. For example, a pressure of less than 5 Pa is sufficient to generate the desired perfusion flow rates. This pressure is very difficult to work with, as it is easily overwhelmed, for example, by changes in hydrostatic head caused by fluid moving from an input reservoir to an output reservoir. For example, 1 cm of fluid-height change corresponds to around 100 Pa of pressure change.

The theory relating flow rate to fluidic resistance and pressure differential comes from the Euler Principle:

$$\Delta P = R \cdot Q$$

where $\Delta P$ is the differential pressure, Q is the flow rate, and R is the fluidic resistance. In other words, the fluidic resistance is the parameter that determines how much flow resistance when a pressure is applied (under a given pressure, higher resistance yields a lower flow rate). Euler's Principle applies under laminar flow conditions and predicts a linear relation between the three parameters.

In order to make the fluid-pumping system more robust, less sensitive to the fluid levels in the reservoirs, and easier to control, pressures of 500 Pa and up are preferable. Accordingly, the system increases the fluidic resistance of system to be much to be higher than that of the OOC device 10 alone. To accomplish this, systems in accordance with the present disclosure add one or more fluidic resistors in-line with the OOC device 10 to be perfused.

An additional advantage of using a resistor that dominates the flow's fluidic resistance and is substantially higher than that of the OOC device 10 is that the flow rate is then less dependent on variations in the chip's fluidic characteristics. In particular, flow rates are less susceptible to chip-to-chip or channel-to-channel variations (e.g. in manufacture) or to changes during operation (e.g. due to cell growth or bubbles).

Figure 2:
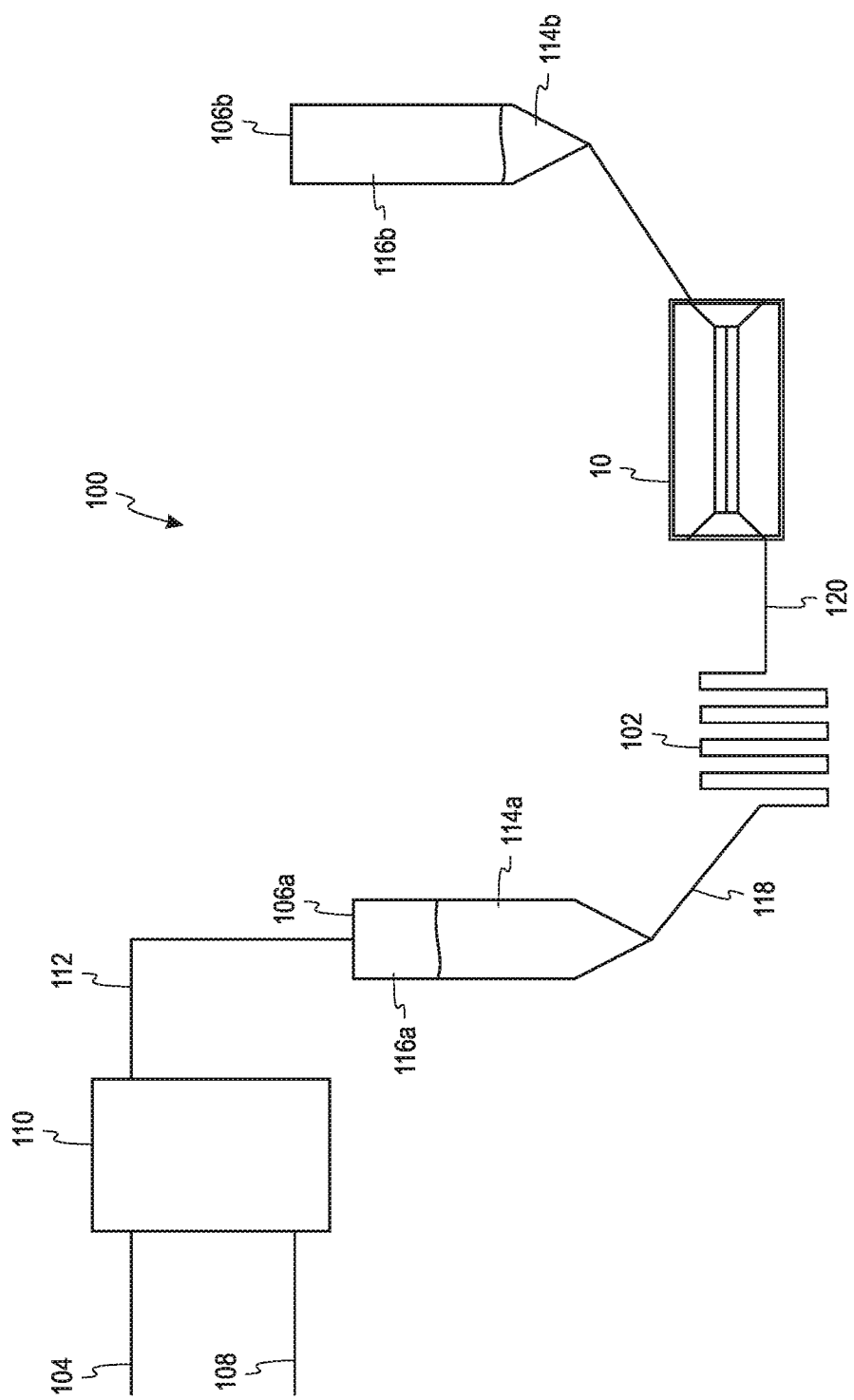
FIG. 2 is a schematic representation of a microfluidic system having a fluid-resistance element, according to aspects of the present disclosure.

FIG. 2 is a schematic representation of a microfluidic system 100 for monitoring a biological function associated with cells that includes a fluid-resistance element 102. The microfluidic system includes a pump mechanism 104, an input fluid reservoir 106a, and output fluid reservoir 106b, a fluid-resistance element 102, and an OOC device 10. The pump mechanism 104 includes a pressure source 108 and a pressure regulator 110. The pressure source 108 supplies the system 100 with compressed gases. The pressure regulator 110 controls the amount of the compressed gases supplied to the system using, for example, a valve (not shown). In some embodiments, the valve is actuated between an open state and a closed state. In the open state, the compressed gases are supplied to the system 100. In the closed state, the valve inhibits the compressed gases from being supplied to the system 100. In some embodiments, the valve includes a closed state and more than one open state. The more than one open states provide a variable amount of compressed gases to the system, for example, the valve being 25% open, 50% open, and the like.

The pump mechanism 104 is coupled to the input fluid reservoir 106a using a gas line 112. The input fluid reservoir 106a contains a working fluid 114a and a pressurized gas 116a. The working fluid 114a is a desired fluid such as media or suspensions of cells, particulates, proteins, chemicals, combinations thereof, or the like. Or the working fluid may expose the cells of the OOC device 10 to a contaminant, pollutant, or pharmaceutical to determine the how the cells react to such exposure. The pressurized gas 116a applies a pressure to the working fluid 114a to move the working fluid 114a out of the input fluid reservoir 106a and to the fluid-resistance element 102 and the OOC device 10.

Selection of a specific gas for use as the pressurized gas 116a has significance because it may dissolve into the working fluid 114a. Additionally, dissolving too much gas into the biological liquid increases the risk of forming and accumulating bubbles within the device. This problem is exacerbated by higher applied pressures. In order to mitigate or eliminate this problem, the gas used to apply pressure to the working fluid 114a may be selected appropriately. For example, helium can be used as the pressurized gas 116a, or as a component thereof, because helium's solubility in water is very low (assuming the working fluid 114a is predominantly water). Additionally or alternatively, the pressurized gas 116a can be formulated according to the needs of the cell culture. For example, 5% $CO_2$ in air is a typical mixture. In some embodiments, where the nominal set-pressure is 20 kPa, a mixture of about 20% helium and 80% the 5% $CO_2$-air mixture can be used, so that the partial pressure of 5% $CO_2$-air mixture remains at or under what the partial pressure at atmospheric pressure.

The input fluid reservoir 106a is coupled to the fluid-resistance element 102 using a fluid line 118. The fluid-resistance element 102 provides a fluidic resistance to the working fluid 114a that is substantially larger than the fluid resistance associated with the OOC device 10. In some embodiments, the fluid resistance of the fluid-resistance element 102 is greater than about 10, 20, 100, 500, 5000, or 50000 times the resistance of the OOC device 10. This fluid resistance results in a pressure drop or head loss of the working fluid 114a across the fluid-resistance element 102 prior to entering the OOC device 10. Beneficially, this provides for modularity of the system 100 as fluid-resistance elements 102 can be interchanged to accommodate differing operating conditions of the pump mechanisms 104 and OOC devices 10. As will be described below with reference to FIGS. 3A-4, the fluid-resistance element 102 can be, for example, a channeled resistor 302 or a tubular resistor 402.

The fluid-resistance element 102 is coupled to the OOC device 10 using a fluid input line 120. As describe above with respect to FIG. 1, the OOC device 10 is configured to simulate a biological function associated with cells, such as simulated organs, tissues, etc. One or more properties of the working fluid 114a may change as the working fluid 114a is passed through the microchannels 24, 26 of the OOC device 10 to produce the effluent 114b. As such, the effluent 114b is still the working fluid 114a, but its properties and/or constituents may change when passing through the OOC device 10. The effluent 114b is collected by the output fluid reservoir 106b for collection and later analysis.

FIG. 3A is a schematic representation of a channeled fluid-resistance element 302 that is separate from the OOC device 10. The channeled fluid-resistance element 302 includes a microfluidic channel 304 in a substrate 306. The microfluidic channel 304 can be formed from a number of known processes such as milling, blow-forming, hot embossing, injection molding, etc. The resistance provided by the channeled fluid-resistance element 302 can be selected by using the length and/or cross-sectional area of the microfluidic channel 304, as well as other features such as number of corners, number and size of restrictions and expansions, cross-sectional shape, etc. For example, increasing the length of the channel, decreasing the cross-sectional area, or increasing the number of turns made by the channel will increase the fluidic resistance provided by the fluid-resistance element 302. Beneficially, channeled fluid-resistance elements 302 can be mass produced using known techniques to provide consistent resistances between elements and, thus, systems.

The channeled fluid-resistance element 302 is coupled to the OOC device 10 using fluid input line 120. The fluid input line 120 can be, for example, capillary tubing, an interconnect adapter, or any suitable device to transmit the working fluid 114a from the fluid resistance element 302 to the OOC device 10.

The channeled fluid-resistance element 302 can be configured to be removably connected to, for example, a cartridge. The cartridge provides a user-friendly interface between the system and OOC device 10. In some embodiments, the cartridge removably receives the OOC device 10. In some embodiments, the fluid-resistance element 302 is removably attached to the cartridge, and the OOC device 10 is removably coupled to the fluid-resistance element 302. This allows a variety of fluid-resistance elements to be used with a single cartridge, thus reducing system costs.

Alternatively, the channeled fluid-resistance element 302 can be integrally formed with the cartridge that is configured to hold one or more OOC devices 10. Integrating the fluid-resistance element 302 provides for a more user-friendly, monolithic cartridge.

FIG. 3B is a schematic representation of a channeled fluid-resistance element 302 that is a part of the organ-on-chip device 10', according to aspects of the present disclosure. The OOC device 10' includes an integral channeled fluid-resistance element 302 and fluid input line upstream from the first microchannel 24. Beneficially, incorporating the channeled fluid-resistance element 302 on the OOC device 10 reduces the number of connections to be made within the system, thus reducing the points of failure and increasing user-friendliness.

Figure 4:
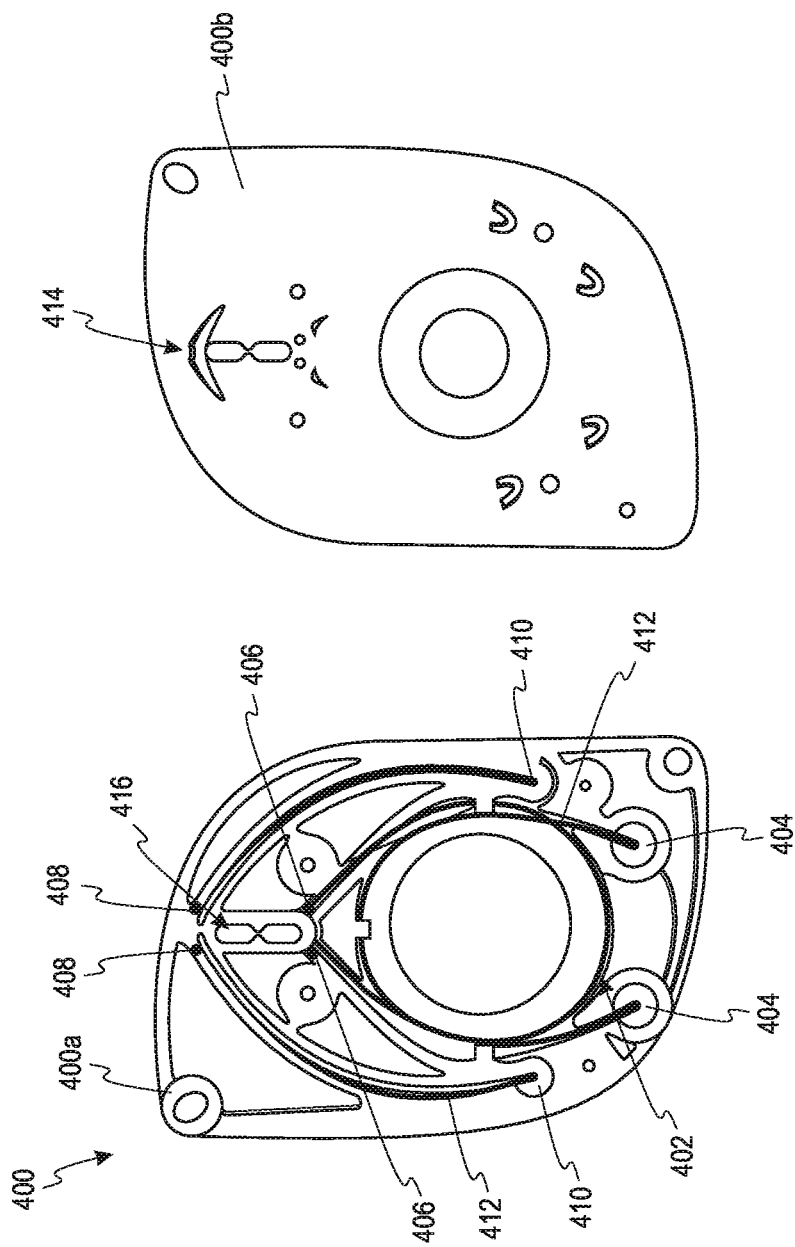
FIG. 4 illustrates a cartridge assembly including a tubular fluid-resistance element, according to aspects of the present disclosure.

FIG. 4 illustrates a cartridge assembly 400 having a tubular fluid-resistance element 402, according to aspects of the present disclosure. The cartridge assembly 400 includes housing having a top side 400a and a bottom side 400b that couple together to form the outer shell of the cartridge assembly 400. The top side 400a includes system-side input ports 404, chip-side input connectors 406, chip-side output connectors 408, and system-side output ports 410. Each system-side input port 404 is coupled to a respective chip-side input connector 406 using a length of capillary tubing 412. Each chip-side output connector 408 is coupled to a respective system-side output port 408 using a length of capillary tubing 412. The bottom side 400b includes a plurality of apertures configured to receive features such as the chip-side inlet connectors 406, chip-side outlet connectors 408, alignment features, or fasteners therethrough.

When assembled, an OOC device 10 is coupled to the chip-side input connectors 406 and the chip-side output connectors 408 using, for example, removable coupling. Beneficially, the capillary tubing 412 can be used as the chip-side input connectors 406 and mate directly with ports of the OOC device 10. The system-side input ports 404 receive the working fluid 114a from the system 100. The working fluid 114a is transferred to the OOC device 10 using capillary tubing 412. This length of capillary tubing 412 provides the fluid-resistance element 402 by including several windings that increase the length of capillary tubing 412 between the system-side input port 404 and the chip-side input connecter 406. This increased length provides a relatively larger pressure drop prior to the working fluid 114a entering the OOC device 10.

The cartridge assembly 400 can further include features to assist in experimentation such as an illumination aperture 416. The illumination apertures are disposed adjacent the OOC device 10 and allow light to pass therethrough, providing for a variety of optical and spectroscopic techniques to be used.

Beneficially, the cartridge assembly 400 includes a modular design and provides reconfigurable fluid resistance. For example, the fluid resistance can be altered by replacing the capillary tubing with tubing having a different diameter. Additionally or alternatively, the fluid resistance can be altered by replacing the capillary tubing with tubing having a different length. Capillary tubing 412 that is compatible with the cartridge assembly 400 is widely available, and comes in a variety of sizes and materials. Beneficially, an end-user may replace the capillary tubing 412 to quickly, easily, and cheaply produce a cartridge assembly 400 with a different fluid resistance. Additionally, the round cross-sectional area of capillary tubing 412 is more advantageous for bubble clearance than non-round cross-sectional profiles.

As shown in FIG. 5A, a bubble 502 may accumulate or get trapped at an interface 504, e.g., a tube-to-chip interface between, for example, the cartridge and the OOC device 10. This bubble accumulation may lower performance of the device, for example, by increasing fluidic resistance, or by dislodging and entering the cell-culture area. In some embodiments, this trapping or accumulation is reduced using a "sharpened" tip, for example, a cone. One example of a sharpened tip is shown in FIG. 5B. Surprisingly, this sharpened tip reduces bubble trapping or accumulation at the port as compared to a blunt tip despite increasing both the hydrophobic surface area of the tip and the volume for the bubbles to become trapped. It was discovered that this is because the bubble must maintain its fixed contact angle with the hydrophobic material, and it is energetically preferred that the bubble is pushed off the surface, rather than the bubble bending its interface to wet the angled surface. This surprising result is more even more pronounced at an inlet. The tubing can either be manufactured with a conical or sharpened tip, or processed to provide such shapes after manufacture. This sharpened tip can also be beneficial at other points of the system, such as where the capillary tubing 412 meets the system-side output ports 410.

In some embodiments, the trapping or accumulation of a bubble is reduced using hydrophilic surfaces. These surfaces are less likely to trap or accumulate a bubble because they prefer to remain wetted by the aqueous liquid. The hydrophilic surface can be formed, for example, by forming the nozzles from hydrophilic materials. Examples of hydrophilic materials that can be used are: glass, certain grades of polystyrene, polypropylene, or acrylic. Additionally or alternatively, the nozzles can be treated to make them hydrophilic, for example, using a coatings, plasma treatment, etc.

FIG. 6 is a flow-rate correlation graph of an example microfluidic system 100 having a fluid-resistance element 102. The fluidic-resistance element 102 is a tubular resistor formed from polyetheretherketone ("PEEK") tubing having an internal diameter of 100 μm, and a length of 235 mm. As shown by the graph, the static pressure of the system is approximately 0.2 kPa. The flow rate increases linearly with increasing supply pressure. Beneficially, the fluidic-resistance element 102 allows supply pressures in the order of Kilopascals to be used, while limiting achieved flow rates through the OOC device 10 on the order of a few microliters per minute. For example, a supply pressure of 6 kPa can be used to deliver the working fluid 114a to the OOC device 10 at a rate of about 6 μL/min.

Providing for the use of a relatively high supply pressure allows for commercial "off-the-shelf" pumps and supplies to be used to drive the system. Additionally, disposing the fluidic-resistance element 102 between the input reservoir 106a and the OOC device 10 allows the dampening of flow fluctuations due to system effects such as regulator or pump pulsatility. Beneficially, the fluidic-resistance element 102 also makes it such that hydrostatic head, such as the head produced by the height of liquid in the fluid reservoirs 106a,b, is small contributor to the flow rate.

Referring again to FIG. 2, a number of pump mechanisms 104 may be used in accordance with the present disclosure. These pump mechanisms 104 can include pressure-driven configurations or displacement-driven configurations. In some embodiments, the pressure-driven configuration includes a pressure regulator. The pressure regulator can be set to apply a desired pressure onto the working fluid 114a. The applied pressure generally corresponds to the desired flow rate through the OOC device 10. Beneficially, electrically controlled pressure regulators such as the SMC ITV line of regulators, manufactured by SMC Corporation (Tokyo, Japan), enable control of the pressure and, indirectly, flow rate using, for example, a computer.

In some embodiments, the displacement-driven configuration includes volumetric pumps such as a syringe pump or a two-port pump such as a peristaltic pump, piezo pump, braille pump, etc. The volumetric pumps are configured to deliver a predetermined volumetric flow of gas to the input reservoir 106a. Unfortunately, delivering the gas at a constant volumetric flow may require long periods of time for the system to build up the needed pressure because the volumetric flow of operation will be relatively low. In some embodiments, the volumetric pump and/or other components of the system are filled with a substantially incompressible fluid. This reduces the gas volume, thus requiring less action to build up the needed pressure. Additionally or alternatively, as will be described below with respect to FIGS. 12-13, a pressure sensor can be used to monitor the generated pressure, and the pump can be set to a first volumetric flow rate that is higher than the second, operating flow rate in order to build the pressure to the predetermined set point. Advantageously, use of two-port pumps does not require the reciprocation that the syringe pump requires and, thus, the two-port pump may continue without interruption.

Surprisingly, pressure-driven systems can be modified to allow for organ linking e.g., interconnecting multiple OOC devices 10 together in series. This is because the canonical pressure-driven system is a "one-port pump", e.g. lacking separate input and output ports like a peristaltic pump. Beneficially, a moveable cap, which normally seals the fluid reservoir 106a and opens as needed to allow, for example, an autosampler to access the fluid reservoir. More details on the autosampler can be found in International Patent Application No. PCT/US14/46439, filed Jul. 11, 2014, which is owned by the assignee of the present application and is incorporated by reference in its entirety.

FIG. 7A illustrates a moveable-cap assembly 700 having a pressure line 702 disposed therethrough, according to aspects of the present disclosure. The movable-cap assembly 700 includes a cap member 704 configured to pivot about a hinge 706. The cap member includes a gasket 708 configured to form a substantially air-tight seal with the fluid reservoir 106a. When not receiving a sample of media, the movable-cap assembly 700 is sealed to the input fluid reservoir 106a, and the input fluid reservoir 106a is pressurized by the pressure line 702. When receiving a sample, the cap member 704 pivots about the hinge 706 to release the seal of the fluid reservoir 106a. After the sample is deposited, the cap member 704 pivots about the hinge 706 to seal the fluid reservoir 106a once again. The pressure line 702 then supplies pressure to the input fluid reservoir 106a until the input fluid reservoir 106a reaches a desired pressure. Beneficially, the pressure line 702 being disposed through the cap member provides for the movable-cap assembly 700 and pressure line 702 to be part of the autosampler or other instrument that interfaces with the cartridge, rather than the cartridge itself. This simplifies the design of the cartridge, as well as providing a convenient cartridge-to-system interface requiring fewer connections. FIG. 7B illustrates a moveable-cap assembly 700' having a pressure line disposed 702' within the reservoir input reservoir 106a, according to aspects of the present disclosure.

FIG. 8A is a schematic diagram of a microfluidic system 800a having two fluid-resistance elements 102, each operatively coupled to a respective microfluidic channel of a single OOC device 10. In this embodiment, the pressurized gas 116a applies pressure to the working fluid 114a. The working fluid 114a is transferred to the fluid-resistance elements 102 through a respective fluid line 118. Each fluid-resistance element 102 is coupled to a respective channel of the OOC device 10 using a fluid-input line 120. It is contemplated that the fluid-resistance elements 102 can be selected to have different fluidic resistances, thereby resulting in different flow rates through the microfluidic channels.

FIG. 8B is a schematic diagram of a microfluidic system 800b having two fluid-resistance elements 102, each operatively coupled to a respective microfluidic channel of separate organ-on-chip devices 10. The working fluid 114a is transferred to the fluid-resistance elements 102 through a respective fluid line 118. Each fluid-resistance element 102 is coupled to a respective channel of a respective OOC device 10 using a fluid-input line 120. It is contemplated that the fluid-resistance elements 102 can be selected to have different fluidic resistances, thereby resulting in different flow rates through the different OOC devices 10.

FIG. 8C is a schematic diagram of a microfluidic system 800c having one fluid-resistance element 102 operatively coupled to multiple microfluidic channels. As shown, the multiple microfluidic channels may be included on one or more OOC devices 10. The working fluid 114a is transferred to the fluid-resistance element 102 through a fluid line 118. The fluid-resistance element 102 is coupled to two channels of a first OOC device 10 using a respective fluid-input line 120, and is coupled to a channel of a second OOC device 10 using a fluid-input line 120. Beneficially, use of several OOC devices 10 in parallel with only one pressure regulator leads to better data by helping to ensure the OOC devices 10 or microfluidic channels 24, 26 are exposed to the same conditions.

While a number of measures are taken to inhibit the bubble accumulation and trapping within microfluidic systems, it is generally impossible to completely prevent the accumulation of bubbles over the duration of typical experiments, especially upon initial filling of the system. Flushing cycles, or periods of pumping at higher rates or pressures, can be used in order to remove bubbles that have become trapped in the system. However, this flushing has potential drawbacks. First, each of the OOC devices 10 has a pumping rate that is defined by shear rates and other physiologically relevant parameters that limit the duration and intensity of a flushing cycle. Additionally, the longer the flushing cycle, the more media is pumped through the microfluidic system, which undesirably leads to a more dilute effluent that makes quantitative chemical and biological readouts more difficult. To address these drawbacks, systems in accord with the present disclosure may include monitoring mechanisms to determine a general flow rate throughout the system. From this, an accumulation of bubbles can be detected and a flushing cycle can be selectively actuated.

Figure 9:
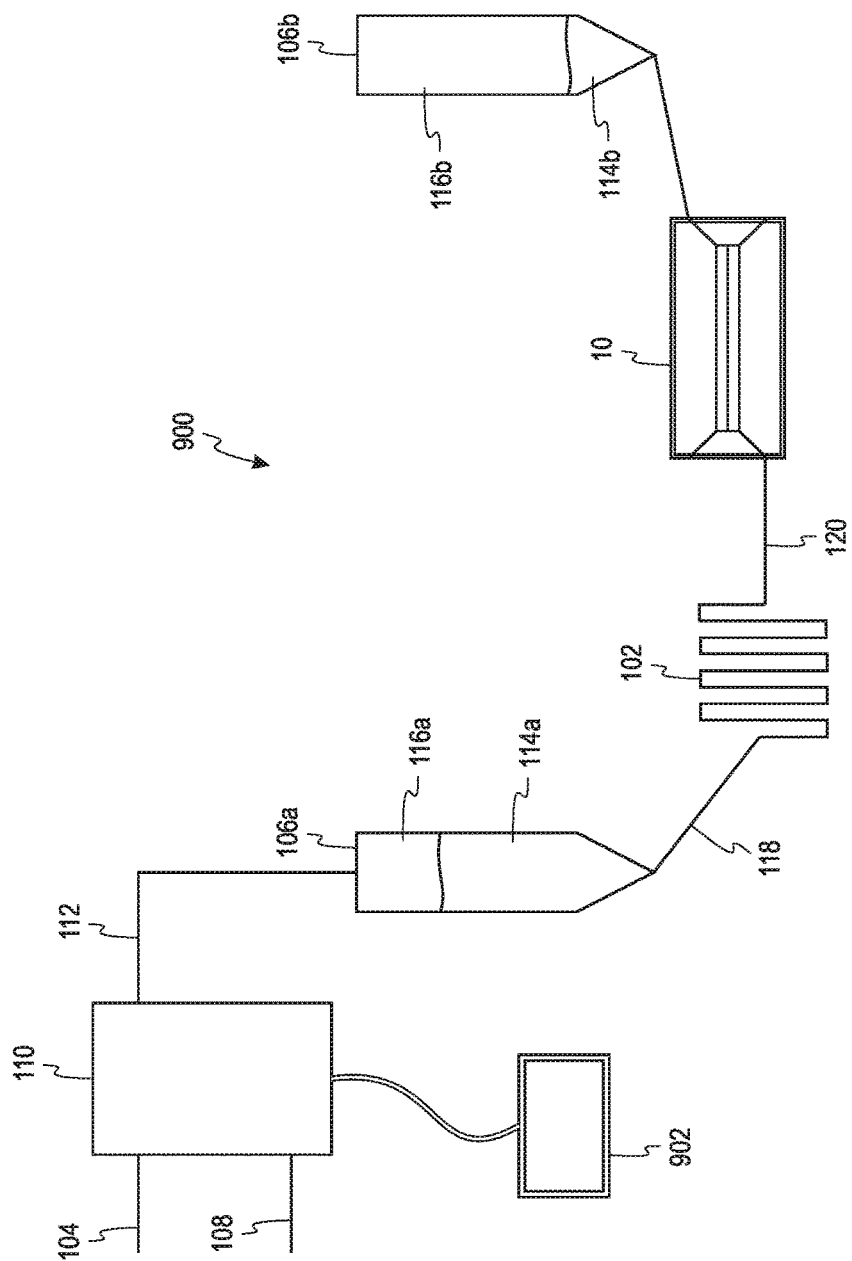
FIG. 9 illustrates a schematic diagram of a microfluidic system having a valve-monitoring component, according to aspects of the present disclosure.

FIG. 9 illustrates a schematic diagram of a microfluidic system having a valve-monitoring component 902. Pressure regulators 110 use a pressure source 108 having a relatively high-pressure gas, and transfer quantities of the high-pressure gas to the output (e.g., gas line 112) via a valve (not shown). In some embodiments, the valve is actuated between an open state and a closed state, such as a solenoid valve. The period of transfer of gas to the output results in the output having a new gas pressure that is lower than the relatively high-pressure gas. In some embodiments, the valve includes a closed state and more than one open state, such as the valve being 25% open, 50% open, and the like. The level that the valve is open, e.g., 25% open, also affects the new gas pressure because the head loss across the valve is altered and, in turn, the quantity of gas transferred to the output is altered. For example, over a given time period, a valve that is 25% open will have greater head loss and transfer less gas than a valve that is 50% open.

The valve-monitoring component 902 is coupled to the pressure regulator 110 of the pump mechanism 104, and is configured to monitor one or more properties associated with the valve. In some embodiments, the one or more properties monitored includes the period of time between valve openings, the percentage of time that the valve is opened, the amount that the valve is opened, combinations thereof, and the like. This monitoring can be done in a variety of ways, such as monitoring the electronic control signal sent to the valve. These properties can then be associated with an estimated flow-rate of the system. For example, relatively higher liquid flow rates require the pressure reservoir to be replenished more frequently (or with higher gas flow), which causes the valve to open more. Beneficially, the relationship between flow rate and the monitored parameter does not require a simple relationship, such as a linear relationship, but rather any monotonic relation between can be accounted for through use of, for example a lookup table.

Figure 10:
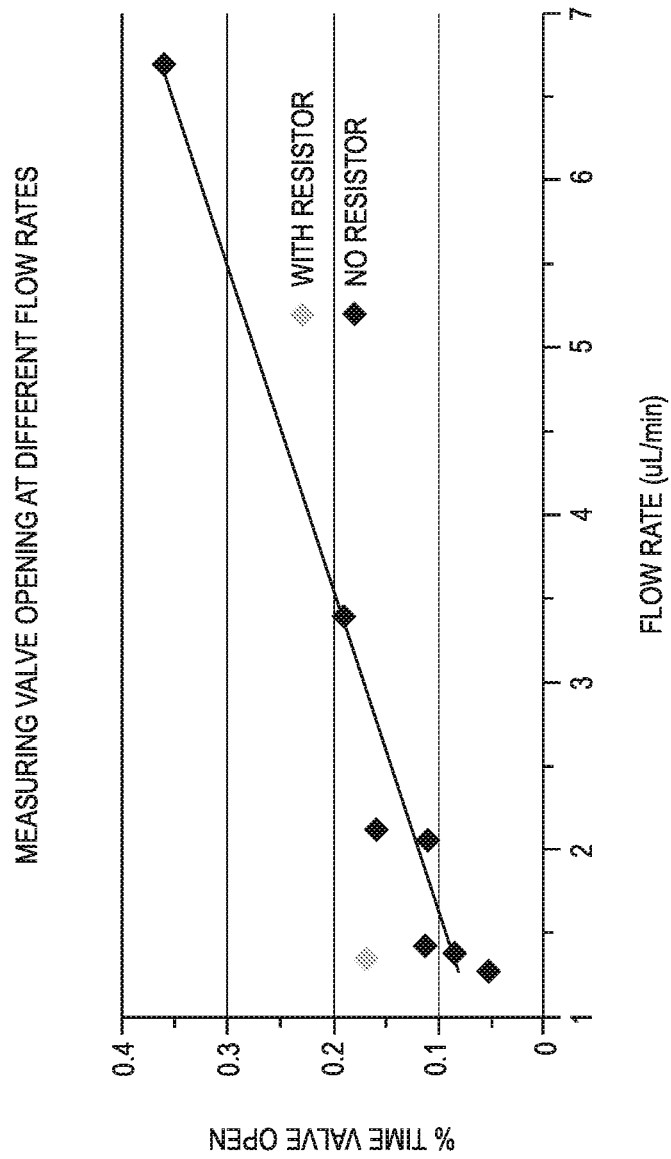
FIG. 10 is an exemplary correlation graph of flow rate versus the percentage of time that the pressure valve is open, according to aspects of the present disclosure.

FIG. 10 is an exemplary correlation graph of flow rate versus the percentage of time that the pressure valve is open. In this embodiment, the time that the valve remains open is monitored and is compared to the total time monitored. As shown, the percentage of time that the valve is open has a linear relationship with the fluid flow rate through the system. While the illustrated correlation can provide a general quantitative result, a quantitative result is not necessary for this method to be of value. For example, in a system including multiple OOC devices 10, one of the OOC devices 10 may become blocked by air bubbles or debris and decrease the overall flow rate of the system. Beneficially, only modest fidelity is needed to monitor the control signal because the blockage of one OOC device 10 would cause a significant reduction in flow rate, e.g., by one-third. In some embodiments, the blockage of one OOC device 10 in a group of three has been detected in systems having a minimal flow rate (e.g., 1 µL/min nominal flow rate) through each OOC device 10.

Beneficially, the sensitivity of the sensor can be increased by adding one or more elements with high fluidic resistance between the pressure regulator 110 and the input reservoir 106a. By adding the one or more elements with high fluidic resistance, the valve remains open for longer periods of time and/or opens more frequently. These increases increase the sensitivity of detection without having to increase the fidelity or sampling time of the valve-monitoring component 902. In some embodiments, the high fluidic resistance element is a filter, which is described with reference to FIG. 11 below.

Figure 11:
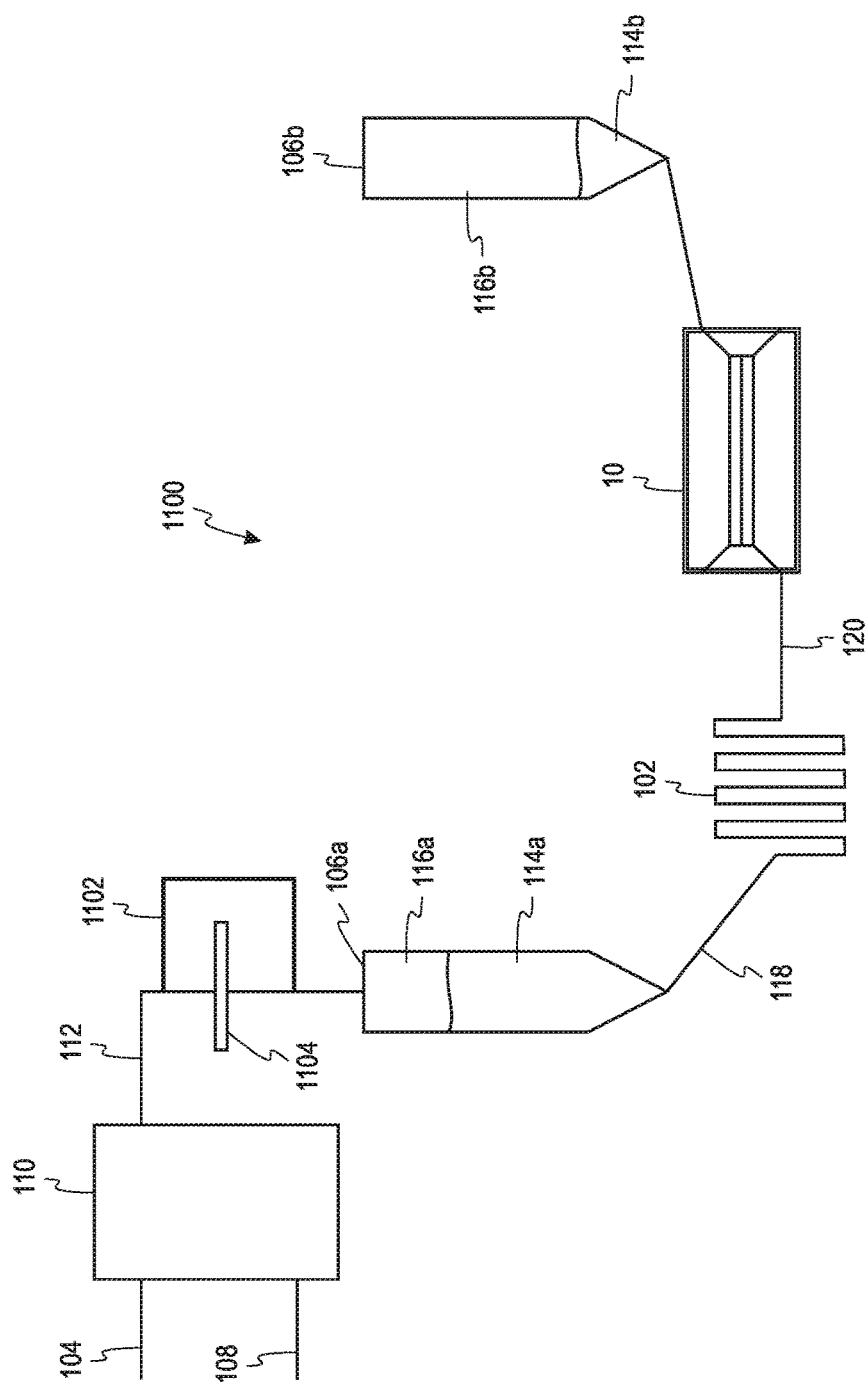
FIG. 11 illustrates a schematic diagram of a microfluidic system having a pressure-differential monitoring mechanism, according to aspects of the present disclosure.

FIG. 11 illustrates a schematic diagram of a microfluidic system 1100 having a pressure-differential monitoring mechanism, according to aspects of the present disclosure. The differential monitoring mechanism includes a pressure-differential monitoring mechanism 1102 disposed about an element of high resistance 1104. As shown, the element of high resistance 1104 is a gas filter, which is often used to increase the purity of the desired gas that comes in contact with the working fluid 114a. The pressure-differential monitoring mechanism 1102 monitors a pressure drop across the high-fluidic-resistance element 1104. Because factors such as the supplied pressure and the filter resistance are generally known, the pressure drop can be correlated to flow in the system 1100. Beneficially, the higher operating pressure of the pump mechanism 104 provides for use of readily available pressure-differential monitoring mechanisms 1102 that cannot be used with typical microfluidic systems. In some embodiments, the fidelity of the pressure-differential monitoring mechanism 1102 is about 5 kPa, 1 kPa, or 0.5 kPa. Beneficially, high-fluidic-resistance elements 1104 such as filters are included in microfluidic systems to ensure sterility. These existing filter locations provide a convenient location for installing the pressure-differential monitoring mechanism 1102.

During operation, there is a slight, average pressure drop across the resistive element that might be measurable, depending on the fidelity of the pressure-differential monitoring mechanism 1102 used. If the entire system becomes clogged, fluid flow would stop and the pressure would equilibrate across the high-fluidic-resistance element 1104, resulting in zero differential pressure. Similarly, if one microfluidic channel in parallel with the one or more other channels becomes clogged, the pressure drop across the high-fluidic-resistance element 1104 would decrease as the total flow rate decreases. The measured differential pressure may require some processing in order to relate to the liquid flow rate because the gas flow rate may be intermittent or uneven due to, for example, discrete openings of the pressure value. In this example, an average or running average and a lookup table can be used to determine a general liquid flow rate of the system.

Figure 12:
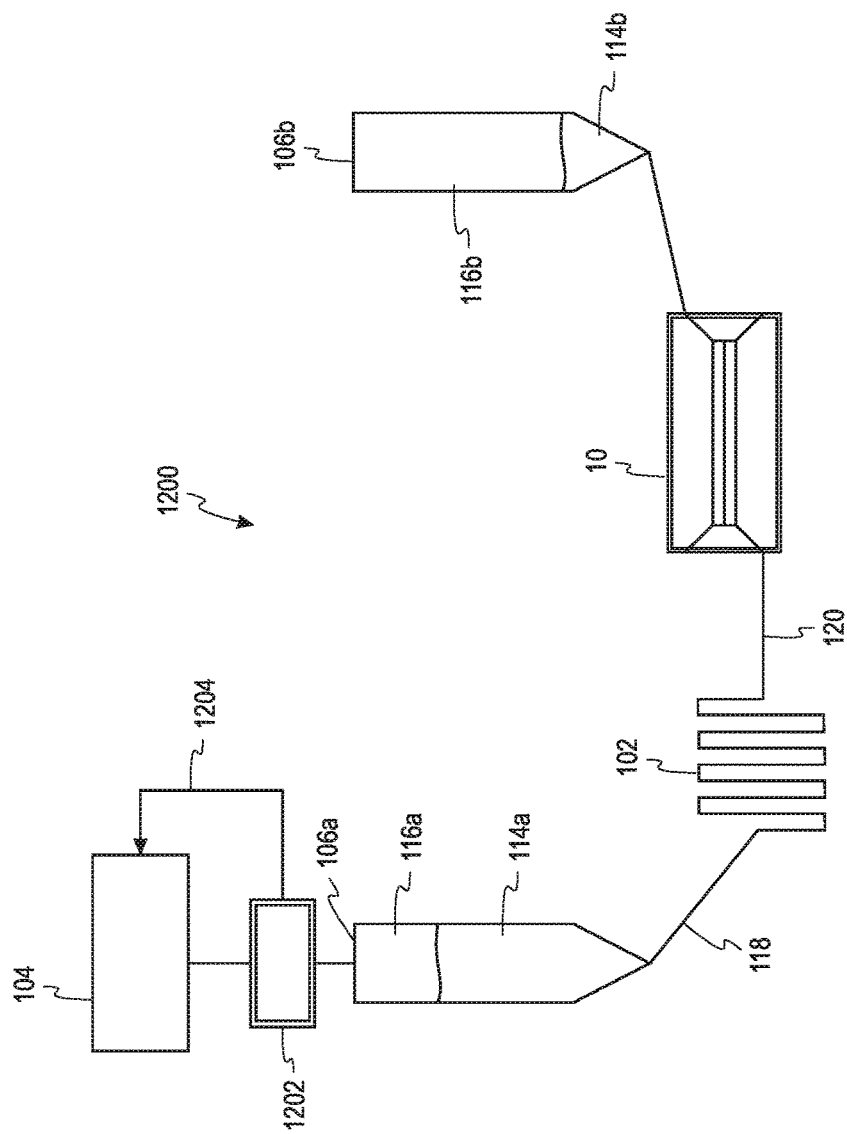
FIG. 12 illustrates a schematic diagram of a microfluidic system having a pressure sensor and feedback loop, according to aspects of the present disclosure.

FIG. 12 illustrates a schematic diagram of a microfluidic system 1200 having a pressure sensor 1202 and feedback loop 1204. The pump mechanism 104 includes a displacement-driven configuration that is used to deliver a volume of gas to the input reservoir 106a, thereby pressurizing the input reservoir 106a. The pressure sensor 1202 is disposed between the pump mechanism 104 and provides feedback on the pressure generated for a given flow rate via the feedback loop 1204. Accordingly, both the flow-rate and pressure are directly observable in this system.

The pressure required to attain a particular flow rate within the system 1200 can be predicted with some degree of accuracy. Thus, so long as the system is operating nominally, the flow rate and pressure should fall in line with each other. Because both quantities are directly observable in this system, this condition is easily verified, and any deviation from the pressure/flow-rate relation could indicate an obstruction, leak, or other system failure. This is a very powerful source of feedback, and it could be used to detect or diagnose a variety of conditions with high accuracy. Beneficially, the system can be actuated to more-selectively remedy these system failures. In some embodiments, the volumetric pump moves only when the system pressure falls below a predetermined threshold. The volumetric pump can be monitored for movement to determine whether a blockage has occurred. A blockage may be indicated by the measured system pressure remaining generally constant, but the pump not moving for a period of time. To remove the blockage, the predetermined threshold may be raised to a second, higher pressure to increase the system pressure and clear the blockage.

Figure 13:
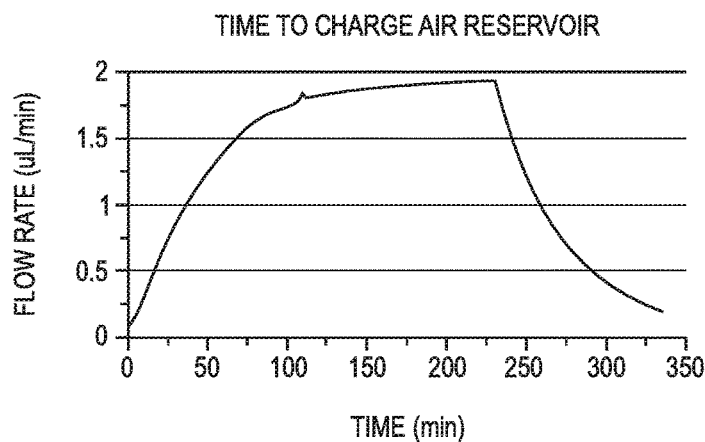
FIG. 13 is a graph of liquid flow rate over time in an exemplary system having a continuous volumetric flow rate of supply gas.

FIG. 13 is a graph of liquid flow rate over time in an exemplary system having a continuous volumetric flow rate of supply gas. To generate the graph, a syringe pump set at a constant rate of 2 µL/min was used to supply gas to the system. As shown, at this constant flow rate, it took approximately two hours for the liquid flow rate to reach 90% of the gas flow rate. Beneficially, this time can be dramatically reduced by setting the syringe pump to a first, higher volumetric flow rate, for example 1 mL/min, and monitoring the pressure of the system. When the pressure reaches a first predetermined value, the syringe pump can be reduced to a second, lower volumetric flow rate, for example, 2 µL/min. In some embodiments, the second volumetric flow rate is approximately equal to the volumetric flow rate of the working fluid 114a through the system. In some embodiments, the first volumetric flow rate is about 10 times greater than the second volumetric flow rate. In some embodiments, the first volumetric flow rate is about 100 times greater than the second volumetric flow rate. In some embodiments, the first volumetric flow rate is about 1000 times greater than the second volumetric flow rate. In one example, the ramp-up time is reduced from about 2 hours to about 1.5 minutes using the first and the second volumetric flow rates. Beneficially, such a reduction in ramp-up time reduces the amount of lag time for experiments, as well as the quality of the experimental data. It is contemplated that more sophisticated control strategies may be used to set the syringe rates, for example, proportional-integral-derivative control, a subset thereof, or the like.

An additional problem that arises with bubble accumulation or debris accumulation is accumulation at inputs, outputs, or within components of the system can stop flow entirely and lead to critical, sometimes irreversible failure of the system. Moreover, without special action, the system may be unable to remove the obstruction and recover without special action. For example, the system may not include a set point that is high enough to overcome the pinning action on the obstruction.

Figure 14:
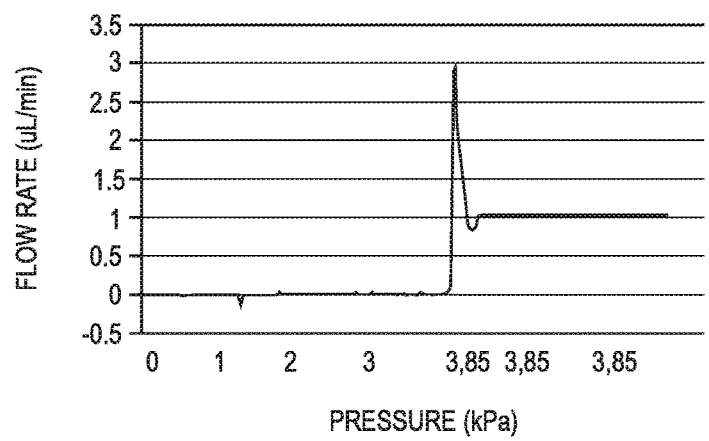
FIG. 14 is a graph of flow-rate as pressure is increased for a bubble-impinged system.

FIG. 14 is a graph of flow-rate as pressure is increased for a bubble-impinged system. As is shown, the flow rate of the system remains zero until the pinning action is overcome at 3.85 kPa. After this point, the flow rate returns to the nominal flow rate expected for a pressure of 3.85 kPa. Thus, if the set point for the nominal flow rate of the system requires less than 3.85 kPa, the obstruction would never be cleared and the system would fail.

Beneficially, the pressure applied to the system can follow pressure-modulation profile that will assist in clearing accumulations of bubbles and/or debris prior to those accumulations obstructing the entire system. Additionally or alternatively, a pressure-modulation profile can be used that will assist in clearing an accumulations of bubbles and/or debris that have obstructed the entire system. The pressure-modulation profile applies a desired pressure for a predetermined amount of time, and then, periodically, increases the applied pressure to a second desired pressure for a period of time before returning to the first desired pressure.

Figure 15:
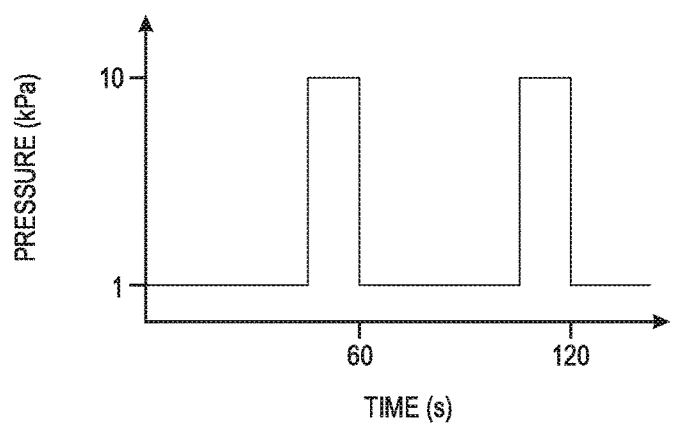
FIG. 15 illustrates an example pressure-modulation profile, according to aspects of the present disclosure.

FIG. 15 illustrates an example pressure-modulation profile, according to aspects of the present disclosure. In the illustrated example, a pressure of 1 kPa is applied to yield the desired nominal flow rate through the system. Periodically, the pressure is increased to a predetermined level for a short period of time. In the illustrated embodiment, the predetermined level of 10 kPa is used to clear any obstructions from the system. The periodic cycle occurs about once every minute, and the predetermined pressure is applied for about five seconds. Beneficially, use of pressure-modulation profiles allows for clearing obstructions from the system, without significantly increasing the cost of the system with flow-rate monitors and the like. Moreover, use of pressure-modulation profiles allows for clearing obstructions from the system without proactive action. Further, coordinated modulation of pressures in two microfluidic channels in an OOC device 10 may be helpful where the channels are linked by a porous membrane.

FIG. 16 is a system 1600 including an input reservoir 106a, a pressure source 1602, an OOC device 10, and an output reservoir 106b. In the illustrated embodiment, the pressure source 1602 is coupled to the fluid line between the input reservoir 106a and the OOC device 10. The pressure source 1602 is configured to increase the volumetric flow rate of the fluid into the OOC device 10. The pressure source 1602 is coupled to a controller (not shown) that controls operation of the pressure source 1602. In some embodiments, the pressure source 1602 is a pump such as a volumetric pump. The pressure source 1602 applies a force to move the fluid from the upstream input reservoir 106a toward the 00C device 10. In some embodiments, the pump is in direct communication with the working fluid. For example, a volumetric pump may be placed in direct communication with the fluid such that the pump acts on a length of capillary tubing containing the fluid to displace the fluid and move a volume of the fluid downstream. As the frequency that the pressure is applied increases or decreases (e.g., increasing or decreasing the r.p.m. of a peristaltic pump), the flow rate similarly increases or decreases.

FIG. 17 illustrates an example modulated flow profile having periodic flushing cycles in the system 1600 of FIG. 16 that are triggered at predetermined times by the pressure source 1602. This modulated flow profile can also be applied to other microfluidic systems mentioned above in FIGS. 1-15. In the illustrated embodiment, the system 1600 periodically transitions between a normal operating mode and a flushing mode. As shown, the flow rate of the fluid is increased when transitioning from the normal operating mode to the flushing mode, and is decreased when transitioning from the flushing mode to the normal operating mode.

In the illustrated embodiment of FIG. 17, the flow rate during the normal operating mode α remains generally constant during the experiment. At a predetermined first time X, the flow rate of the system is increased from the normal operating flow rate α to the flushing flow rate β. This ramp-up in flow rate can be caused by, for example, increasing the speed of a pump or increasing the pressure driving the fluid. The system remains at the flushing flow rate β for a predetermined period of time, and then returns to the normal operating mode at the normal operating flow rate a. The system then proceeds in normal operating mode until reaching a second predetermined time Y, at which point the flushing cycle is triggered again. In some embodiments, the flushing flow rate is at least ten times higher than the operating flow rate. In some embodiments, the flushing flow rate at least 100 times higher than the operating flow rate. In some embodiments, the flushing cycle is triggered at consistently spaced time intervals.

During operation in the normal condition, an undesired aggregation (e.g., bubbles) will form at a first point in the fluid path. The flow properties of the fluid path may be such that the aggregation will not grow only to a certain point, and will not grow to fully occlude the fluid path. The flushing cycle is configured to cause at least a portion of the undesired aggregation to move from the first position toward a second, downstream position. Beneficially, movement of the undesired aggregation through the fluid path will occur due to the flushing cycle even if that aggregation is not detectable by, for example, sensors.

In some embodiments, the normal operating mode proceeds for between about two and about eight hours. In some embodiments, the normal operating mode proceeds for between about two hours and about six hours. In some embodiments, the normal operating mode proceeds for about four hours. In some embodiments, the flushing cycle lasts for between about five seconds and about 120 seconds. In some embodiments, the flushing cycle lasts for between about ten and about ninety seconds. In some embodiments, the flushing cycle lasts for between about 20 seconds and about 75 seconds. For example, surprisingly, systems that operated in the normal operating mode for four hours, then entered a flushing cycle that lasted a duration of between twenty and seventy-five seconds before returning to the normal operating mode were able to consistently maintain the viability and function of lung-on-a-chip devices for more than seven days of perfusion.

In some embodiments, flushing of adjacent fluid paths is triggered simultaneously to inhibit damage to components of the system. For example, the fluid paths for the first microchannel 24 and the second microchannel 26 of the 00C device 10 can be flushed at the same time even though one of the fluid paths may not need to be flushed as frequently. Beneficially, the simultaneous flushing reduces stress to the membrane 30 between the microchannels by reducing or maintaining the pressure differential across the membrane 30 during the flushing cycle.

It is contemplated that the normal operating flow rate α may increase or decrease by known amounts during operation depending on the particular experimental design. This known increase and/or decrease during normal operating mode can be accounted for, and characteristics such as the period between flushing cycles, the difference in flow rate between the normal operating mode and the flushing mode, the duration of the flushing mode, combinations thereof, and/or the like can be altered to account for these known changes in the operating modes.

It is further contemplated that systems and methods in accord with the present invention may include sensors to monitor characteristics associated with the fluid line such as flow rate, pressures, etc. For example, a sensor can be used to directly or indirectly detect the existence of a triggering condition such as a bubble or bubbles in the system. A control mechanism can then be used to trigger a flushing cycle that is in addition to, or in place of, the periodic flushing in response to the triggering condition. In some embodiments, an optical bubble sensor is used to directly determine development of a bubble within the flow path. In some embodiments, a flow-rate sensor is used to detect the presence of a bubble by detecting augmented flow resistance (e.g., by detecting an unexpected change in flow rate or pressure).

Measurement and analysis of flow characteristics and/or triggering of additional flushing cycles can be used to adjust the time period between flushing cycles, adjust the flow rate used during the flushing cycle, adjust the duration of the flushing cycle, etc. In some embodiments, the detection of a bubble and initiation of a non-periodic flush will cause the system to reduce the time period between flushing cycles. In some embodiments, the detection of unexpected flow characteristics during normal operation mode will cause the system to increase the flow rate used during the flushing cycle or increase the duration of the flushing cycle.

While many of the above-described examples of increasing or decreasing flow through the system have been made with reference to increasing or decreasing pump speed or driving pressures, it is contemplated that valves may be used in the system to provide control of flow rates. For example, valves, particularly microfluidic valves, can be used to constrict or extend fluid paths, leading to lower or higher flow rates of the working fluid.

While pressure-driven aspects of the present invention have been described as applying pressure to push the working fluid 114a through the system, in some embodiments, a vacuum is applied to the output reservoir 106b to pull the working fluid 114a through the system. In such a case, the fluid-resistance element 102 still permits better control of the fluid flow as the working fluid is drawn to the input reservoir. Further, this allows a wider range of pressurized gases to be used because the pressurized gas is in contact with the working fluid 114a after it has been in contact with the cells within the 00C device 10. Moreover, if a vacuum is applied to the output reservoir 106b in combination with pressurized gas 116a applied to the input reservoir 106a, a wider range of pressurized gases can be used because the vacuum will outgas the effluent 114b.

While FIGS. 2, 9, 11, and 12 reference the output fluid reservoir 106b having a gas 116b at atmospheric pressure, it is contemplated that higher pressures may also be used.

Beneficially, the output reservoir 106b having the gas 116b at a higher pressure provides for the system to operate at a higher overall pressure. This higher operating pressure across the system may provide beneficial properties, such as the system more closely replicating selected biological conditions, for example biological conditions of the kidneys.

While the input fluid reservoir 106a and output fluid reservoir 106b have been described as storing the fluid in bulk, it is contemplated that capillary reservoirs may additionally or alternatively be used. A capillary reservoir includes an elongated fluid path. The elongated fluid path is configured to store the working fluid 114a therein. Beneficially, this elongated fluid path can be configured to inhibit mixing of the working fluid 114a between sample inputs. That is, the elongated fluid path beneficially retains time-based differences between samples injected in the reservoir at a first time, and samples injected at a second time. This provides additional sensitivity to the data collected by the system.

While FIGS. 2-4, 8A-9, and 11-12 depict the fluid-resistance element 102 as disposed upstream from the OOC device 10, it is contemplated that other configurations may be used. In some embodiments, the resistor is disposed downstream from the OOC device 10. Beneficially, this can provide for higher operating pressures for the OOC device 10. This higher operating pressure across the OOC device 10 may provide beneficial properties, such as the OOC device 10 more closely replicating selected biological conditions, for example, biological conditions of the kidneys. In some embodiments, fluid-resistance elements 102 are disposed both upstream and downstream from the OOC device 10. Beneficially, disposing fluid-resistance elements 102 on both the upstream and downstream of the OOC device 10 provide for a wider range of pressures to be used at the input fluid reservoir 106a and the output fluid reservoir 106b.

FIGS. 9-15 have been described with reference to OOC devices 10 and microfluidic devices generally. However, the advantages of these systems are not limited to microfluidic applications, but extend to other fluid systems.

Beneficially, systems having pressure-driven flow can be easily modified, or even used as-is, to also pump gas through the one or more microchannels on the OOC devices 10. This is useful, for example, for lung-on-chip airway channels, where the pushed gas can be used to clear the airway channels of liquids or to perfuse it with air to simulate breathing. In some embodiments, separate regulators are used, but share a supply line, thus reducing the costs and complexity of the system.

According to some embodiments of the present invention, a system for monitoring a biological function associated with cells comprises:
 (a) a microfluidic device having a first microchannel, a second microchannel, and a membrane located at an interface region between the first microchannel and the second microchannel, the membrane including a first side facing toward the first microchannel and a second side facing toward the second microchannel, the first side having the cells adhered thereto;
 (b) a fluid line for delivering a working fluid to or from the first microchannel from or to, respectively, a fluid reservoir; and
 (c) a fluid-resistance element coupled to the fluid line, the fluid-resistance element having a first fluidic resistance that is substantially larger than a second fluidic resistance associated with the first microchannel.

Optionally, the fluid reservoir includes the working fluid and a pressurized gas. The pressurized gas the flow of the working fluid through the fluid line and fluid-resistance element.

Optionally, the fluid-resistance element includes a chip having an elongated fluid path. The first fluidic resistance is created by the elongated fluid path.

Optionally, the fluid-resistance element includes an elongated capillary tube has an elongated fluid path. The first fluidic resistance is created by the elongated fluid path.

Optionally, the capillary tube undergoes multiple windings within a housing of the fluid-resistance element.

Optionally, a system or device may further include a pump mechanism to apply pressure to a gas within the fluid reservoir, thereby creating a pressurized gas.

Optionally, the gas is substantially insoluble in the working fluid.

Optionally, the gas is a mixture of gases, the mixture including a gas that is substantially insoluble in the working fluid.

Optionally, the first fluidic resistance is at least about 100 times greater than the second fluidic resistance.

Optionally, the fluid reservoir includes an elongated fluid path. The elongated fluid path is configured to store the working fluid therein.

According to other embodiments of the present invention, a device for monitoring a biological function associated with cells comprises:
 (a) a body having a first microchannel, a second microchannel, and a membrane located at an interface region between the first microchannel and the second microchannel, the membrane including a first side facing toward the first microchannel and a second side facing toward the second microchannel, the first side having the cells adhered thereto;
 (b) the body further defining an internal fluid-resistance element coupled to the first microchannel, the internal fluid-resistance element having a first fluidic resistance that is substantially larger than a second fluidic resistance associated with the first microchannel.

Optionally, the first fluidic resistance is at least about 100 times greater than the second fluidic resistance.

According to further embodiments of the present invention, a system for monitoring a biological function associated with cells comprises:
 (c) a microfluidic device having a first microchannel, a second microchannel, and a membrane located at an interface region between the first microchannel and the second microchannel, the membrane including a first side facing toward the first microchannel and a second side facing toward the second microchannel, the first side having the cells adhered thereto;
 (d) a fluid reservoir having a working fluid and a pressurized gas;
 (e) a pump mechanism in communication with the fluid reservoir to maintain a desired pressure of the pressurized gas; and
 (f) a fluid-resistance element located within a fluid path between the fluid reservoir and the first microchannel, the fluid-resistance element having a first fluidic resistance that is substantially larger than a second fluidic resistance associated with the first microchannel.

Optionally, the fluid-resistance element includes a substrate having an elongated fluid path. The first fluidic resistance is created by the elongated fluid path.

Optionally, the fluid-resistance element includes an elongated capillary tube having an elongated fluid path. The first fluidic resistance is created by the elongated fluid path.

Optionally, the capillary tube undergoes multiple windings within a housing of the fluid-resistance element.

Optionally, the system or device may further include a pressure sensor within the fluid reservoir, the pump mechanism being actuated in response to a predetermined output from the pressure sensor.

Optionally, the fluid resistance element is located upstream of the first microchannel.

Optionally, the fluid resistance element is located downstream from the first microchannel.

Optionally, the first fluidic resistance is at least about 100 times greater than the second fluidic resistance.

According to yet another embodiment of the present invention, a system for monitoring a biological function associated with cells comprises:
(g) a microfluidic device having a first microchannel, a second microchannel, and a membrane located at an interface region between the first microchannel and the second microchannel, the membrane including a first side facing toward the first microchannel and a second side facing toward the second microchannel, the first side having the cells adhered thereto;
(h) a fluid reservoir having a working fluid and a pressurized gas, the fluid reservoir being coupled to the first microchannel via a fluid line;
(i) a pressure regulator in communication with the fluid reservoir to maintain a desired pressure of the pressurized gas, the pressurized gas causing the working fluid to move through the first microchannel; and
(j) a sensor for monitoring activity of the pressure regulator to determine an increase in fluidic resistance within the fluid line or the first microchannel.

Optionally, the system or device may further include a fluid-resistance element located within a fluid path between the fluid reservoir and the first microchannel. The fluid-resistance element has a first fluidic resistance that is substantially larger than a second fluidic resistance associated with the first microchannel.

Optionally, the sensor monitors one or more properties associated with a valve of the pressure regulator.

Optionally, the one or more properties is a percentage of time that the valve is open.

Optionally, the sensor monitors a control signal sent to the valve.

Optionally, the system or device may further include a gas filter located in a gas line between the pressure regulator and the fluid reservoir. The sensor measures the pressure differential across the gas filter.

Optionally, the increase in fluidic resistance is caused by bubbles in the fluid line or the first microchannel.

Optionally, the increase in fluidic resistance is caused by a blockage in the fluid line or the first microchannel.

Optionally, the blockage is associated with cells in the first microchannel.

Optionally, the pressure regulator, in response to the sensor determining the increase in fluidic resistance, maintains a second pressure of the pressurized gas, the second pressure being selected to clear a blockage.

According to other embodiments of the present invention, a system for monitoring a biological function associated with cells comprises:
(k) a microfluidic device having a first microchannel, a second microchannel, and a membrane located at an interface region between the first microchannel and the second microchannel, the membrane including a first side facing toward the first microchannel and a second side facing toward the second microchannel, the first side having the cells adhered thereto;
(l) a fluid reservoir having a working fluid and a pressurized gas, the fluid reservoir being coupled to the first microchannel via a fluid line;
(m) a volumetric pump in communication with the fluid reservoir to cause a pressure on the pressurized gas, the pressurized gas causing the working fluid to move through the first microchannel; and
(n) a sensor located between the fluid reservoir and the volumetric pump, the sensor for monitoring the pressure of a gas in the system.

Optionally, in response to the pressure being below a predetermined value, the volumetric pump supplies gas to the fluid reservoir at a first volumetric flow rate. And wherein, in response to the pressure being at or above the predetermined value. The volumetric pump supplies gas to the fluid reservoir at a second volumetric flow rate. The second volumetric flow rate is less than the first volumetric flow rate.

Optionally, the second volumetric flow rate is approximately equal to a volumetric flow rate of the working fluid through the first microchannel.

Optionally, the first volumetric flow rate is at least about 100 times greater than the second volumetric flow rate.

According to yet other aspects of the present invention, a system for monitoring a biological function associated with cells comprises:
(o) a microfluidic device having a first microchannel, a second microchannel, and a membrane located at an interface region between the first microchannel and the second microchannel, the membrane including a first side facing toward the first microchannel and a second side facing toward the second microchannel, the first side having the cells adhered thereto;
(p) a fluid reservoir having a working fluid and a pressurized gas, the fluid reservoir being coupled to the first microchannel via a fluid line, the pressurized gas causing the working fluid to move through the first microchannel;
(q) a pressure source in communication with the fluid reservoir to provide a pressure-modulation profile, the pressure-modulation profile including periodic pressure increases to inhibit the accumulation of bubbles or debris in the system.

According to another aspect, the present invention involves a method of monitoring a biological function in a device having a membrane located on an interface region between a first microchannel and a second microchannel. A first side of the membrane faces the first microchannel receiving a working fluid and has a first type of cells adhered thereto. The method comprises:
(r) in response to applying pressure to a gas within a fluid reservoir containing the gas and the working fluid, moving the working fluid through a fluid-resistance element; and
(s) after moving the working fluid through the fluid-resistance element, transferring the working fluid into the first microchannel.

Optionally, the fluid-resistance element has a first fluidic resistance that is substantially larger than a second fluidic resistance associated with the first microchannel.

Optionally, the first fluidic resistance is at least 100 times greater than the second fluidic resistance.

Optionally, the fluid-resistance element is located within the device in fluid path prior to the first microchannel.

According to yet another aspect, the present invention also involves a method of detecting a fluid blockage in a microfluidic device having a membrane located on an interface region between a first microchannel and a second microchannel. The first side of the membrane faces the first microchannel receiving a working fluid and has a first type of cells adhered thereto. The method comprises:
- (t) in response to applying pressure to a gas within a fluid reservoir contain the gas and the working fluid, moving the working fluid though the first microchannel; and
- (u) monitoring an activity of a pressure source that provides pressure to the gas.

Optionally, the monitoring includes monitoring a valve that is associated with the pressure source.

Optionally, the monitoring includes monitoring the pressure differential across a filter located in a gas line between the pressure regulator and the fluid reservoir.

Optionally, the monitoring includes monitoring movement of a volumetric pump, the volumetric pump being configured to move when the pressure to the gas is below a predetermined threshold.

Optionally, the method may further include raising, in response to the volumetric pump not moving for a period of time, the predetermined threshold to a second predetermined threshold.

According to yet a further aspect, the present invention includes a method of inhibiting an accumulation of bubbles within a microfluidic system having a device with a membrane located at an interface region between a first microchannel and a second microchannel. The first side of the membrane faces the first microchannel receiving a working fluid and has a first type of cells adhered thereto. The microfluidic system includes a fluid line with a fluid-resistance element leading to the first microchannel within the device. The method comprises:
- (v) in response to applying pressure to a gas within a fluid reservoir containing the gas and the working fluid, moving the working fluid through the fluid-resistance element and into the first microchannel; and
- (w) periodically increasing the pressure to the gas within the fluid reservoir to advance bubbles through the first microchannel and the fluid line.

Optionally, the pressure is increased to a level known to remove bubbles from the system by opening a valve that is associated with the pressure source.

Optionally, the periodic increase in pressure occurs at one cycle per minute.

According to other aspects of the present invention, a microfluidic system comprises:
- (x) a microfluidic device having a first microchannel;
- (y) a fluid reservoir;
- (z) a fluid line for delivering a working fluid to or from the first microchannel from the fluid reservoir; and
- (aa) a fluid-resistance element within the fluid line, the fluid-resistance element having a first fluidic resistance that is substantially larger than a second fluidic resistance associated with the first microchannel.

In yet another aspect of the present invention, a microfluidic system comprises:
- (bb) a microfluidic device having a first microchannel;
- (cc) a fluid reservoir having a working fluid and a pressurized gas;
- (dd) a pump in communication with the fluid reservoir to maintain a desired pressure of the pressurized gas; and
- (ee) a fluid-resistance element located within a fluid path between the fluid reservoir and the first microchannel, the fluid-resistance element having a first fluidic resistance that is substantially larger than a second fluidic resistance associated with the first microchannel.

According to yet a further aspect of the present invention, a fluid system comprises:
- (ff) a device having a first channel for receiving a working fluid;
- (gg) an input-fluid reservoir for holding the working fluid;
- (hh) a output-fluid reservoir for holding the working fluid after the working fluid has passed through the device;
- (ii) a fluid line for delivering the working fluid from the input-fluid reservoir and to the output-fluid reservoir, the device being coupled to the fluid line; and
- (jj) a fluid-resistance element within the fluid line, the fluid-resistance element having a first fluidic resistance that is substantially larger than a second fluidic resistance associated with the first channel.

According to some other configurations of the present invention, a fluid system comprises:
- (kk) a device having a first channel for receiving a working fluid;
- (ll) a fluid reservoir for holding the working fluid and a pressurized gas;
- (mm) a fluid line coupling the fluid reservoir and the device;
- (nn) a pump in communication with the fluid reservoir to maintain a desired pressure of the pressurized gas so as to transfer the working fluid through the device; and
- (oo) a fluid-resistance element within the fluid line, the fluid-resistance element having a first fluidic resistance that is substantially larger than a second fluidic resistance associated with the first channel.

According to yet a further aspect, the present invention is a method for inhibiting formation of an occlusion in a microfluidic system that comprises:
- (pp) flowing a working fluid through the microfluidic system at a first flow rate for a first time period, an undesired aggregation of bubbles forming at a first position in the microfluidic system during the first time period;
- (qq) in response to the first time period ending, increasing a flow rate of the working fluid to a second flow rate for a second time period to cause at least a portion of the undesired bubbles to move from the first position toward a second position; and
- (rr) repeating the acts of flowing and increasing to cause a periodic bubble flushing within the microfluidic system.

Optionally, the method may further include:
- (ss) measuring characteristics of the microfluidic system;
- (tt) in response to the measuring, adjusting at least one of the first time period and the second time period during the repeating.

Optionally, the adjusted first time period is longer than the initial first time period.

Optionally, the increasing is caused by a pump in direct communication with the working fluid.

Optionally, the method may further include:
- (uu) measuring characteristics of the microfluidic system; and
- (vv) in response to the measuring, adjusting the second flow rate during the repeating.

Optionally, the adjusted second flow rate is greater than the initial second flow rate.

Optionally, the method may further include:
(ww) measuring, during the first time period, characteristics of the microfluidic system;
(xx) analyzing the characteristics of the microfluidic system for an occurrence of a triggering condition;
(yy) in response to the triggering condition, causing the working fluid to flow through the microfluidic system at a third flow rate;
(zz) after the response to the triggering condition, returning the flow of the working fluid through the microfluidic system to the first flow rate.

Optionally, the acts of causing the working fluid to flow through the microfluidic system at the third flow rate and the returning the working fluid to the first flow rate do not affect the ending of the first time period.

Optionally, the third flow rate is equal to the second flow rate.

Optionally, the triggering condition is the detection of a bubble.

Optionally, the undesired aggregation of bubbles at the first position abuts at least one cell.

According to yet another aspect of the present invention, a system for monitoring a biological function associated with cells comprises:
(aaa) a microfluidic device having a microchannel including a surface, the cells being adhered to the surface;
(bbb) a pressure source configured to cause a working fluid to flow along a fluid path that includes the first microchannel of the microfluidic device; and
(ccc) a controller coupled to the pressure source and causing the pressure source to be operable in a normal operating mode and a flushing mode, the normal operating mode including the working fluid flowing past the cells within the microchannel at a first flow rate, the flushing mode including the working fluid flowing past the cells within the microchannel at a second flow rate that is higher than the first flow rate to move an undesired aggregation of bubbles from a first position in the fluid path toward a second position along the fluid path, the controller switching to the flushing mode in response to a predetermined condition.

Optionally, the predetermined condition is a predetermined interval of time.

Optionally, the system or device may further include a sensor for measuring characteristics of the system, wherein the predetermined interval of time is adjusted in response to the measured characteristics.

Optionally, the system or device may further include a sensor for measuring characteristics of the system.

Optionally, the predetermined condition is in response to the sensor detecting a triggering event.

Optionally, the triggering event is sensing the undesired aggregation of bubbles reaching a predetermined threshold.

Optionally, the second flow rate is adjusted in response to the measured characteristics.

Optionally, the pressure source is a pump in direct communication with the working fluid.

Optionally, the pump is a volumetric pump.

Optionally, the undesired aggregation of bubbles at the first position abuts at least one cell.

According to another aspect, the present invention is a method for monitoring a biological function associated with living cells that comprises:
(ddd) flowing a working fluid at known fluid-flow conditions along a fluid path including a microchannel of a microfluidic device during a normal operating mode, the microchannel having cells disposed therein; and
(eee) on a periodic basis during the normal operating mode, automatically flushing the fluid path at a flushing flow rate for a time period to remove at least a portion of an undesired aggregation from the fluid path.

Optionally, the periodic basis is automatically flushing at consistently spaced time intervals.

Optionally, the method is performed for at least seven days.

Optionally, the automatic flushing inhibits cell death due to the undesired aggregation.

Optionally, the undesired aggregation is an accumulation of air bubbles.

Optionally, the flushing flow rate is higher than a first flow rate associated with the normal operating mode.

Optionally, the undesired aggregation would not form an occlusion under continuous flowing of the working fluid in the normal operating mode.

Optionally, the method may further include:
(fff) detecting a presence of a bubble along the fluid path; and
(ggg) in response to the detection and independent of the automatic flushing, flushing the fluid path at a second flushing flow rate.

Optionally, the second flushing flow rate is different from the flushing flow rate.

Optionally, the automatic flushing is caused by a pump in direct communication with the working fluid.

Optionally, the automatic flushing is caused by raising the height of a fluid reservoir holding the fluid reservoir.

Optionally, the automatic flushing is caused by altering a valve within the fluid path.

According to some other aspects of the present invention, a system for monitoring a biological function associated with cells comprises:
(hhh) a microfluidic device having a microchannel;
(iii) a fluid line for delivering a working fluid from a fluid reservoir to or from the microchannel; and
(jjj) a fluid-resistance element coupled to the fluid line, the fluid-resistance element having a first fluidic resistance that is substantially larger than a second fluidic resistance associated with the first microchannel.

Optionally, the fluid reservoir includes the working fluid and a pressurized gas. The pressurized gas forces the flow of the working fluid through the fluid line and fluid-resistance element.

Optionally, the fluid-resistance element includes a chip having an elongated fluid path. The first fluidic resistance is created by the elongated fluid path.

Optionally, the fluid-resistance element includes an elongated capillary tube having an elongated fluid path. The first fluidic resistance is created by the elongated fluid path.

Optionally, the capillary tube undergoes multiple windings within a housing of the fluid-resistance element.

Optionally, the system or device may further include a pump mechanism to apply pressure to a gas within the fluid reservoir, thereby creating a pressurized gas.

Optionally, the gas is substantially insoluble in the working fluid.

Optionally, the gas is a mixture of gases. The mixture includes a gas that is substantially insoluble in the working fluid.

Optionally, the first fluidic resistance is at least about 100 times greater than the second fluidic resistance.

Optionally, the fluid reservoir includes an elongated fluid path, the elongated fluid path being configured to store the working fluid therein.

While the present invention is described with reference to one or more particular embodiments or configurations, those skilled in the art will recognize that many changes may be made thereto without departing from the spirit and scope of the present invention. Each of these embodiments or configurations, and obvious variations thereof, is contemplated as falling within the spirit and scope of the invention. It is also contemplated that additional embodiments according to aspects of the present invention may combine any number of features from any of the embodiments or configurations described herein.

What is claimed is:

1. A system for monitoring a biological function associated with cells, comprising:
   a microfluidic device having a first microchannel, a second microchannel, and a membrane located at an interface region between the first microchannel and the second microchannel, the membrane including a first side facing toward the first microchannel and a second side facing toward the second microchannel, the membrane having living cells adhered thereto; and
   a fluid line for delivering a working fluid to or from the first microchannel from or to, respectively, a fluid reservoir that is disposed outside of the microfluidic device; and
   a cartridge configured to removably receive the microfluidic device, the cartridge comprising a fluid-resistance element having an elongated fluid path, thereby having a first fluidic resistance that is 10-50,000 times greater than a second fluidic resistance associated with the first microchannel.

2. The system of claim 1, wherein the fluid reservoir is configured to have the pressurized gas force the flow of the working fluid through the fluid-resistance element.

3. The system of claim 1, wherein said fluid-resistance element undergoes multiple windings so as to create said elongated path.

4. The system of claim 2, further including a pump mechanism to apply pressure to a gas within the fluid reservoir, thereby creating a pressurized gas.

5. The system of claim 4, wherein the gas is substantially insoluble in the working fluid.

6. The system of claim 4, wherein the gas is a mixture of gases, the mixture including a gas that is substantially insoluble in the working fluid.

7. The system of claim 2, wherein the elongated fluid path is configured to store the working fluid therein.

8. A device for monitoring a biological function associated with cells, comprising:
   a body having a first microchannel, a second microchannel, and a membrane located at an interface region between the first microchannel and the second microchannel, the membrane including a first side facing toward the first microchannel and a second side facing toward the second microchannel, the membrane having living cells adhered thereto;
   the body further defining an internal fluid-resistance element coupled to the first microchannel, the internal fluid-resistance element comprising a substrate having an elongated fluid path, thereby having a first fluidic resistance that is 10-50,000 times greater than a second fluidic resistance associated with the first microchannel.

9. A system for monitoring a biological function associated with cells, comprising:
   a microfluidic device having a first microchannel, a second microchannel, and a membrane located at an interface region between the first microchannel and the second microchannel, the membrane including a first side facing toward the first microchannel and a second side facing toward the second microchannel, the membrane having living cells adhered thereto;
   a fluid reservoir disposed outside of the microfluidic device having a working fluid and a pressurized gas;
   a pump mechanism in communication with the fluid reservoir to maintain a desired pressure of the pressurized gas; and
   a fluid-resistance element located within a cartridge between the fluid reservoir and the first microchannel, the fluid-resistance element comprising a substrate having an elongated fluid path, thereby having a first fluidic resistance that is 10-50,000 times greater than a second fluidic resistance associated with the first microchannel.

10. The system of claim 9, wherein said fluid-resistance element undergoes multiple windings so as to create said elongated path.

11. The system of claim 9, further including a pressure sensor within the fluid reservoir, the pump mechanism being actuated in response to a predetermined output from the pressure sensor.

12. The system of claim 9, wherein the fluid-resistance element is located upstream of the first microchannel.

13. The system of claim 9, wherein the fluid-resistance element is located downstream from the first microchannel.

14. A system, comprising:
   a microfluidic device comprising a first microchannel fluidically coupled to a fluid reservoir comprising a pressurized gas, the fluid reservoir being located outside of the microfluidic device; and;
   a cartridge comprising a fluid-resistance element fluidically coupled to the fluid reservoir and the first microchannel, the fluid-resistance element comprising a substrate having an elongated fluid path thereby having a first fluidic resistance that is 10-50,000 times greater than a second fluidic resistance associated with the first microchannel.

15. The system of claim 14, wherein said fluid path is a capillary channel.

16. The system of claim 14, wherein said microfluidic device further comprises a second microchannel, and a membrane located at an interface region between the first microchannel and the second microchannel.

* * * * *